US009023584B2

(12) United States Patent
Maruyama

(10) Patent No.: US 9,023,584 B2
(45) Date of Patent: *May 5, 2015

(54) RADIATION-SENSITIVE COMPOSITION, AND COMPOUND

(71) Applicant: JSR Corporation, Tokyo (JP)

(72) Inventor: Ken Maruyama, Tokyo (JP)

(73) Assignee: JSR Corporation, Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 13/901,621

(22) Filed: May 24, 2013

(65) Prior Publication Data

US 2013/0280658 A1     Oct. 24, 2013

Related U.S. Application Data

(63) Continuation of application No. PCT/JP2011/076839, filed on Nov. 21, 2011.

(30) Foreign Application Priority Data

Nov. 26, 2010   (JP) .................................. 2010-264360
Oct. 19, 2011   (WO) .................. PCT/JP2011/074080

(51) Int. Cl.
```
G03F 7/004      (2006.01)
G03F 7/027      (2006.01)
C07C 309/00     (2006.01)
C07C 315/00     (2006.01)
C07C 303/00     (2006.01)
C07C 309/27     (2006.01)
C07C 381/12     (2006.01)
G03F 7/039      (2006.01)
G03F 7/20       (2006.01)
```

(52) U.S. Cl.
CPC .............. *G03F 7/004* (2013.01); *C07C 309/27* (2013.01); *C07C 381/12* (2013.01); *C07C 2101/14* (2013.01); *C07C 2102/42* (2013.01); *C07C 2103/74* (2013.01); *G03F 7/0045* (2013.01); *G03F 7/0392* (2013.01); *G03F 7/0397* (2013.01); *G03F 7/2041* (2013.01); *Y10S 430/114* (2013.01); *Y10S 430/128* (2013.01)

(58) Field of Classification Search
USPC ............... 430/270.1, 913, 927; 562/125, 400, 562/109; 568/18, 28; 558/44
See application file for complete search history.

(56) References Cited

U.S. PATENT DOCUMENTS

```
4,454,074  A  *  6/1984   Naylor ........................... 562/100
4,491,628  A     1/1985   Ito et al.
4,910,122  A     3/1990   Arnold et al.
8,173,353  B2 *  5/2012   Masuyama et al. ......... 430/270.1
8,535,812  B2 *  9/2013   Totsuka et al. ................ 428/523
8,597,869  B2 * 12/2013   Sagehashi et al. ......... 430/270.1
2005/0238992 A1* 10/2005  Kodama .................... 430/270.1
2008/0081925 A1*  4/2008  Sakamoto et al. ............... 558/52
2008/0153030 A1*  6/2008  Kobayashi et al. ........ 430/270.1
2008/0187860 A1*  8/2008  Tsubaki et al. ............ 430/270.1
2013/0280657 A1* 10/2013  Kasahara et al. .......... 430/285.1
2014/0005301 A1*  1/2014  Kunimoto et al. ............ 523/400
```

FOREIGN PATENT DOCUMENTS

```
JP         59-45439         3/1984
JP         06-12452 B2      5/1984
JP         59-93448         5/1984
JP         05-188598        7/1993
JP       2000-327654       11/2000
JP       2001-188344        7/2001
JP       2005-004158        1/2005
JP       2009-120762        6/2009
JP       2009120762  A  *   6/2009
JP       2009-258586       11/2009
JP       2009258586  A  *  11/2009
JP       2011026590  A  *   2/2011
WO     WO 2008/047678       4/2008
```

OTHER PUBLICATIONS

Machine translation of JP 2009-258586 (no date).*
Machine translation of JP2000-327654 (no date).*
Written Opinion for corresponding International Application No. PCT/JP2011/074080, Jan. 17, 2012.
"Perfluorooctyl Sulfonates; Proposed Significant New Use Rule", Federal Register, Oct. 18, 2000, p. 62319-62333, vol. 65, No. 202, (2000).
Jiro Nakamura et al., "Resist Surface Roughness Calculated using Theoretical Percolation Model", J. Photopolym. Sci. Tech., 1998, p. 571-576, vol. 11, No. 4.
Eishi Shiobara et al., "Resist Edge Roughness with Reducing Pattern Size", p. 313-323, Proc. SPIE, vol. 3333, (1998).
S. C. Palmateer et al., "Line Edge Roughness in sub-0.18-μm Resist Patterns", p. 634-642, Proc. SPIE, vol. 3333, (1998).

(Continued)

*Primary Examiner* — Amanda C. Walke
(74) *Attorney, Agent, or Firm* — Oblon, McClelland, Maier & Neustadt, L.L.P.

(57) ABSTRACT

A radiation-sensitive composition includes a compound represented by a formula (1), and a polymer having a structural unit that includes an acid-labile group. In the formula (1), $R^1$ represents a group having a polar group; n is an integer of 1 to 4, wherein, in a case where $R^1$ is present in a plurality of number, the plurality of $R^1$s are identical or different, and optionally at least two $R^1$s taken together represent a cyclic structure; A represents an alicyclic hydrocarbon group having a valency of (n+1); and $M^+$ represents a monovalent onium cation.

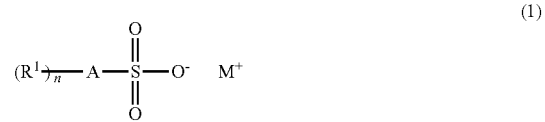

(1)

8 Claims, No Drawings

(56) References Cited

OTHER PUBLICATIONS

Hideo Namatsu et al., "Three-dimensional siloxane resist for the formation of nanopatterns with minimum linewidth fluctuations", J. Vac. Sci. Technol. B16 (1), 1998, p. 69-76.

J. V. Crivello, "Cationic Polymerization—Iodonium and Sulfonium Salt Photoinitiators", Advances in Polymer Science, 1984, p. 1-48, vol. 62.

International Search Report for corresponding International Application No. PCT/JP2011/076839, Feb. 28, 2012.

Office Action issued Oct. 7, 2014 in Japanese Patent Application No. 2012-545753 (with English language translation).

Office Action issued Feb. 3, 2015, in Taiwan Patent Application No. 100143378 filed Nov. 25, 2011 (w/English translation).

* cited by examiner

RADIATION-SENSITIVE COMPOSITION, AND COMPOUND

CROSS-REFERENCE TO RELATED APPLICATIONS

The present application is a continuation application of International Application No. PCT/JP2011/076839, filed Nov. 21, 2011, which claims priority to Japanese Patent Application No. 2010-264360, filed Nov. 26, 2010, and to International Application No. PCT/JP2011/074080, filed Oct. 19, 2011. The contents of these applications are incorporated herein by reference in their entirety.

BACKGROUND OF THE INVENTION

1. Field of the Invention

The present invention relates to a radiation-sensitive composition, and a compound.

2. Discussion of the Background

Miniaturization of structures in various types of electronic devices such as semiconductor devices and liquid crystal devices has been accompanied by demands for miniaturization of resist patterns in lithography processes. Although fine resist patterns having a line width of about 90 nm can be formed using an ArF excimer laser at present, finer pattern formation is required in the future. Chemically amplified type radiation-sensitive compositions that have been broadly used for the present generate an acid upon irradiation with a radioactive ray such as a far ultraviolet light typified by a KrF excimer laser or an ArF excimer laser at light-exposed site, by a reaction with the acid as a catalyst, leading to a change in a rate of dissolution in a developer solution at light-exposed sites, whereby a resist pattern can be formed on the substrate (see Japanese Unexamined Patent Application, Publication No. S59-45439, and Perfluorooctyl Sulfonates; Proposed Significant New Use Rule).

Superior transparency to radioactive rays and a high quantum yield upon generation of an acid are demanded for radiation-sensitive acid generating agent contained in such chemically amplified radiation-sensitive compositions. Furthermore, in order to improve resolution of a radiation-sensitive composition, sufficiently superior strength of the generated acid, and a diffusion distance in the resist film (hereinafter, may be also referred to as "diffusion length") that is short to a certain degree have been considered to be desired. Moreover, characteristics such as a sufficiently high boiling point of the acid generated, and resistance to transpiration during a heating step, etc., have been also desired.

Although a lot of acid generating agents have been developed to date, an acid generating agent that sufficiently meets the requirements described above has not yet been obtained. For example, although a radiation-sensitive acid generating agent having a trifluoromethanesulfonyl structure leads to sufficiently superior strength of the acid generated, the acid will have a low boiling point, and is accompanied by a long diffusion length; therefore, resolving performances of the radiation-sensitive composition are not satisfactory. In addition, a radiation-sensitive acid generating agent having a sulfonyl structure bonded to a great organic group such as a 10-camphorsulfonyl structure leads to a sufficiently high boiling point of the acid generated, and a short diffusion length of the acid is attained; however, a disadvantage of a difficulty in dissolving a radiation-sensitive composition containing the same in solvents generally used is involved.

On the other hand, when control of a line width of a more precise pattern should be executed as in the case in which an intended dimension of a device does not exceed a subhalf micron order, chemically amplified resists are required to be not only superior in the resolution, but also superior in smoothness of the surface of a film after formation of a resist pattern. Inferior smoothness of the surface of a film may result in deteriorated electric characteristics of a finally obtained device due to transfer of an uneven shape of the surface of the film (hereinafter, may be also referred to as "nanoedge roughness") to a substrate in transferring the resist pattern to the substrate by a processing such as etching, consequently leading to unfavorable dimensional accuracy of the pattern (see J. Photopolym. Sci. Tech., p. 571 (1998), Proc. SPIE, Vol. 3333, p. 313, Proc. SPIE, Vol. 3333, p. 634, and J. Vac. Sci. Technol. B16 (1), p. 69 (1998)). A radiation-sensitive composition that is capable of preventing the nanoedge roughness and is superior in controllability of line widths of fine patterns has not been obtained to date.

In view of the foregoing circumstances, development of a radiation-sensitive composition that achieves high resolution, and also achieves superior smoothness of the surface of a film after formation of the resist pattern has been strongly desired.

SUMMARY OF THE INVENTION

According to one aspect of the present invention, a radiation-sensitive composition includes a compound represented by a formula (1), and a polymer having a structural unit that includes an acid-labile group.

In the formula (1), $R^1$ represents a group having a polar group; n is an integer of 1 to 4, wherein, in a case where $R^1$ is present in a plurality of number, the plurality of $R^1$s are identical or different, and optionally at least two $R^1$s taken together represent a cyclic structure; A represents an alicyclic hydrocarbon group having a valency of (n+1); and $M^+$ represents a monovalent onium cation.

According to one aspect of the present invention, a compound is represented by a formula (1).

In the formula (1), $R^1$ represents a group having a polar group; n is an integer of 1 to 4, wherein, in a case where $R^1$ is present in a plurality of number, the plurality of $R^1$s are identical or different, and optionally at least two $R^1$s taken together represent a cyclic structure; A represents an alicyclic hydrocarbon group having a valency of (n+1); and $M^+$ represents a monovalent onium cation.

DESCRIPTION OF THE EMBODIMENTS

The radiation-sensitive composition according to an embodiment of the present invention made for solving the foregoing problems contains:

(A) a compound represented by the following formula (1) (hereinafter, may be also referred to as "compound (A)"); and (B) a polymer having a structural unit that includes an acid-labile group (hereinafter, may be also referred to as "polymer (B)").

wherein, in the formula (1), $R^1$ represents a group having a polar group; n is an integer of 1 to 4, wherein, in a case where $R^1$ is present in a plurality of number, the plurality of $R^1$s are identical or different, or at least a pair of $R^1$s optionally bond to one another to taken together represent a cyclic structure; A represents an alicyclic hydrocarbon group having a valency of (n+1); and $M^+$ represents a monovalent onium cation.

Due to containing the compound (A) having the specific structure, the radiation-sensitive composition of the embodiment of the present invention is superior in sensitivity to radioactive rays and achieves high resolution, and is also superior in smoothness of the surface of a film after formation of the resist pattern. The compound (A) serves as a radiation-sensitive acid generating agent in the radiation-sensitive composition. With respect to the reasons for achieving the characteristics described above: a short diffusion length of the acid generated upon exposure being attained due to the compound (A) having a bulky structure, thereby capable of preventing diffusion of the acid; an enhanced interaction of the compound (A) with a resin, etc., contained in radiation-sensitive composition, due to the compound (A) having a polar group, thereby further preventing diffusion of the acid; and the like may be considered. When diffusion of the acid is thus prevented, dissociation of the acid-labile group of the polymer (B) at light-unexposed site is inhibited, whereby formation of a pattern that is superior in resolution is enabled.

The alicyclic hydrocarbon group represented by A in the above formula (1) has preferably 5 or more and 20 or less carbon atoms. When A represents an alicyclic hydrocarbon group having 5 to 20 carbon atoms, the compound (A) will have a more bulky structure; therefore, a diffusion length of the acid generated can be further appropriately shortened. As a result, the radiation-sensitive composition will be more superior in resolution, and in smoothness of the surface of a film after formation of the resist pattern.

The compound (A) is preferably a compound represented by the following formula (1-A), a compound represented by the following formula (1-B) or a combination thereof.

wherein, in the formulae (1-A) and (1-B), $R^1$ and $M^+$ are as defined in the above formula (1), wherein $M^+$ in the formula (1-A) and $M^+$ in the formula (1-B) are identical or different, and $R^1$ in the formula (1-A) and $R^1$ in the formula (1-B) are identical or different; $m_1$ is 0 or 1; and $m_2$ is an integer of 0 to 2.

According to the radiation-sensitive composition of the embodiment of the present invention, due to A in the above formula (1) representing the above-specified alicyclic structure, a diffusion length of the acid generated can be further appropriately shortened. As a result, the radiation-sensitive composition will be more superior in resolution, and in smoothness of the surface of a film after formation of the resist pattern.

The compound represented by the above formula (1-A) is preferably a compound represented by the following formula (1-A-1), and the compound represented by the above formula (1-B) is preferably a compound represented by the following formula (1-B-1):

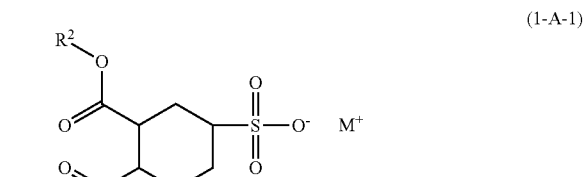

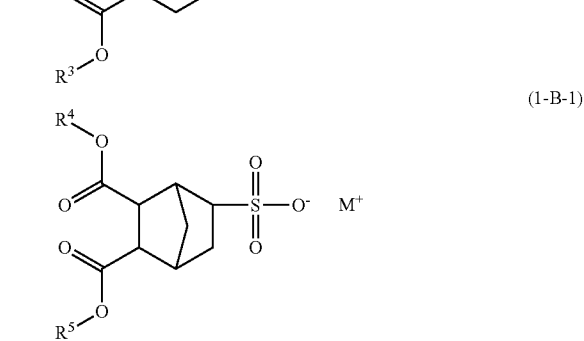

wherein, in the formula (1-A-1) and formula (1-B-1), $R^2$, $R^3$, $R^4$ and $R^5$ each independently represent a linear or branched hydrocarbon group having 1 to 30 carbon atoms, an alicyclic hydrocarbon group having 3 to 30 carbon atoms, an aromatic hydrocarbon group having 6 to 30 carbon atoms, or a heterocyclic group having 4 to 30 carbon atoms, wherein the linear or branched hydrocarbon group may include an ester group, an amide group, a urethane group, a urea group, a carbonate group or a sulfide group between carbon atoms, and a part or all of hydrogen atoms included in the hydrocarbon group, the alicyclic hydrocarbon group, the aromatic hydrocarbon group and the heterocyclic group represented by $R^2$, $R^3$, $R^4$ and $R^5$ are not substituted or substituted; and $M^+$ is as defined in the above formula (1).

The compound (A) contained in the radiation-sensitive composition of the embodiment of the present invention is bulky and highly polar due to $R^1$ being a side chain having an ester bond, whereby diffusion of the acid generated is further prevented. As a result, the radiation-sensitive composition is more superior in resolution and is also more superior in smoothness of the surface of a film after formation of the resist pattern.

It is preferred that the polymer (B) further includes a structural unit represented by the following formula (b-1), a structural unit represented by the following formula (b-2) or a combination thereof.

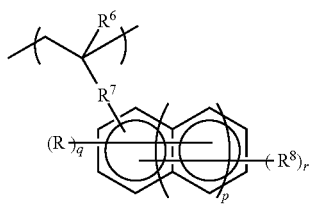
(b-1)

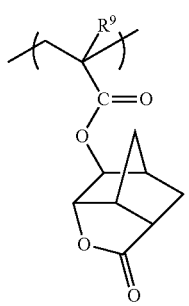
(b-2)

In the formula (b-1), $R^6$ represents a hydrogen atom or a methyl group; $R^7$ represents a single bond, —CO—O—, or —CO—NH—; $R^8$ represents a linear or branched alkyl group having 1 to 12 carbon atoms, a linear or branched alkoxyl group having 1 to 12 carbon atoms, or an acyloxy group having 2 to 12 carbon atoms; R represents a group that includes a hydroxyl group or a hydroxyl group; p is 0 or 1; q and r are each independently an integer of 0 to 3, wherein, in a case where p is 0, the sum of q and r is no greater than 5, and in a case where $R^8$ is present in a plurality of number, the plurality of $R^8$s are identical or different.

In the formula (b-2), $R^9$ represents a hydrogen atom or a methyl group.

When the polymer (B) has the above-specified structural unit in the radiation-sensitive composition of the embodiment of the present invention, an interaction of the polymer (B) with the compound (A) is enhanced. As a result, diffusion of the acid generated from the compound (A) is prevented, whereby resolution and smoothness of the surface of a film after formation of the resist pattern can be also further improved.

It is preferred that: the radiation-sensitive composition further contains (C) a solvent; the solvent (C) includes (C1) at least one compound selected from the group consisting of an ethylene glycol monoalkyl ether acetate and a propylene glycol monoalkyl ether acetate; and the content of the compound (C1) in the solvent (C) is no less than 70% by mass.

When the radiation-sensitive composition further contains the above-specified solvent (C), solubility of the compound (A) and the polymer (B) increases, thereby enabling a more favorable resist pattern to be formed.

A compound according to another embodiment of the present invention is represented by the following formula (1):

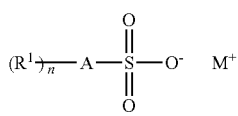

(1)

wherein, in the formula (1), $R^1$ represents a group having a polar group; n is an integer of 1 to 4, wherein, in a case where $R^1$ is present in a plurality of number, the plurality of $R^1$s are identical or different, or at least a pair of $R^1$s optionally bond to one another to taken together represent a cyclic structure; A represents an alicyclic hydrocarbon group having a valency of (n+1); and $M^+$ represents a monovalent onium cation.

It is preferred that the compound of the embodiment of the present invention is represented by the following formula (1-A) or the following formula (1-B):

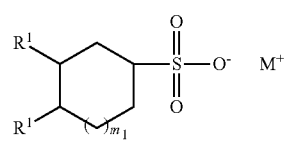
(1-A)

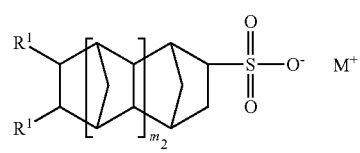
(1-B)

wherein, in the formulae (1-A) and (1-B), $R^1$ and $M^+$ are as defined in the above formula (1), wherein $M^+$ in the formula (1-A) and $M^+$ in the formula (1-B) are identical or different, and $R^1$ in the formula (1-A) and $R^1$ in the formula (1-B) are identical or different; $m_1$ is 0 or 1; and $m_2$ is an integer of 0 to 2.

It is more preferred that the compound of the embodiment of the present invention is a compound represented by the following formula (1-A-1) or the following formula (1-B-1):

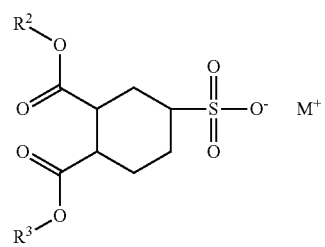
(1-A-1)

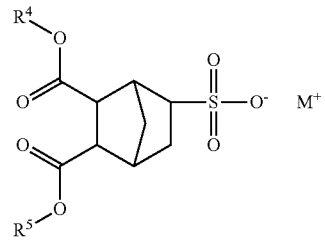
(1-B-1)

wherein, in the formula (1-A-1) and formula (1-B-1), $R^2$, $R^3$, $R^4$ and $R^5$ each independently represent a linear or branched hydrocarbon group having 1 to 30 carbon atoms, an alicyclic hydrocarbon group having 3 to 30 carbon atoms, an aromatic hydrocarbon group having 6 to 30 carbon atoms, or a heterocyclic group having 4 to 30 carbon atoms, wherein an ester group, an amide group, a urethane group, a urea group, a carbonate group or a sulfide group may be included between carbon atoms of the linear or branched hydrocarbon group, and a part or all of hydrogen atoms included in the hydrocarbon group, the alicyclic hydrocarbon group, the aromatic hydrocarbon group and the heterocyclic group represented by $R^2$, $R^3$, $R^4$ and $R^5$ are not substituted or substituted; and $M^+$ is as defined in the above formula (1).

The compound of the embodiment of the present invention is suitably used as an acid generating agent in a radiation-sensitive composition. Since the compound is bulky and polar, a diffusion length of the acid generated upon exposure is controlled to be appropriately short in the radiation-sensitive composition containing the compound as an acid generating agent, whereby smoothness of the surface of a resist film after resolution and pattern formation is also achieved. In addition, due to having a high boiling point, the compound is less likely to be volatilized during a pattern formation process, thereby enabling a favorable pattern to be formed.

It is to be noted that "(meth)acrylate" as referred to herein means "acrylate" or "methacrylate". Also, the term "radiation" in the "radiation-sensitive composition" conceptionally includes a visible light ray, a ultraviolet ray, a far ultraviolet ray, an X-ray, a charged particle ray and the like are involved.

The radiation-sensitive composition of the embodiment of the present invention is efficaciously sensitive to far ultraviolet rays such as a KrF excimer laser, an ArF excimer laser and EUV, X-rays such as a synchrotron radioactive ray, and electron beams, superior in sensitivity, smoothness of the surface of a resist film after resolution and pattern formation (i.e., nanoedge roughness-preventing effect), and capable of forming a fine pattern with high accuracy and in a stable manner. In addition, the compound of the embodiment of the present invention is highly soluble in solvents, and can be suitably used as a radiation-sensitive acid generating agent in the radiation-sensitive composition of the embodiment of the present invention. The embodiments will now be described in detail.

Radiation-Sensitive Composition

The radiation-sensitive composition of an embodiment of the present invention contains (A) a compound and (B) a polymer. In addition, (C) a solvent is contained as a favorable component. Furthermore, the radiation-sensitive composition may contain other optional component as long as desired effects of the embodiment of the present invention are not impaired.

Compound (A)

The compound (A) is represented by the above formula (1). The compound (A) is a radiation-sensitive acid generating agent that generates an acid upon exposure. Due to having high solubilities in solvents, and a high boiling point, the compound (A) is less likely to be volatilized during a photolithography process, and thus effects as an acid generating agent can be sufficiently exhibited. Moreover, due to having a bulky structure, and having a polar group, the compound (A) allows diffusion of a generated acid to be prevented in a resist film. As a result, according to the radiation-sensitive composition containing the compound (A), a favorable resist pattern that is superior in resolution, and a preventive property of nanoedge roughness can be obtained.

In the above formula (1), $R^1$ represents a group having a polar group; n is an integer of 1 to 4, wherein, in a case where $R^1$ is present in a plurality of number, the plurality of $R^1$s are identical or different, or at least a pair of $R^1$s optionally bond to one another to taken together represent a cyclic structure; A represents an alicyclic hydrocarbon group having a valency of (n+1); and $M^+$ represents a monovalent onium cation.

The alicyclic hydrocarbon group having a valency of (n+1) represented by A is preferably an alicyclic hydrocarbon group having 5 to 20 carbon atoms, and specific examples include groups having a structure obtained by removing (n+1) hydrogen atoms from monocyclic hydrocarbon groups such as cyclopentane and cyclohexane, polycyclic hydrocarbon groups such as norbornane, norbornene, tricyclodecane, tetracyclododecane and adamantane, and the like.

Examples of the polar group represented by $R^1$ include an ester group, a carboxyl group, an amide group, a urethane group, a urea group, a carbonate group, a sulfide group, a halogenated alkyl group, a hydroxyl group, a cyano group, a thiol group, a halogen atom, and the like.

The group having a polar group represented by $R^1$ is exemplified by groups obtained by substituting with the polar group a part of hydrogen atoms included in a linear hydrocarbon groups having 1 to 10 carbon atoms or an alicyclic hydrocarbon group having 5 to 20 carbon atoms, R—R'—X—*, wherein, * denotes a site that bonds to A), and the like; R represents a linear hydrocarbon group having 1 to 10 carbon atoms or an alicyclic hydrocarbon group having 5 to 20 carbon atoms; R' represents the polar group; and X represents a single bond, a methylene group, an alkylene group having 2 to 10 carbon atoms, an alicyclic hydrocarbon group having 3 to 30 carbon atoms, or an aromatic hydrocarbon group having 6 to 30 carbon atoms.

The number of the polar group included in $R^1$ may be one, or two or more, and is preferably one. Also, the number of $R^1$ having a polar group included in the compound represented by above formula (1) is preferably 1 to 4, and more preferably 2 to 4.

Furthermore, the monovalent onium cation represented by $M^+$ is exemplified by an onium cation such as O, S, Se, N, P, As, Sb, Cl, Br and I. of these, each onium cation of S and I is preferred.

Specific examples of a sulfonium cation (onium cation of S) include those represented by the following formula (2). Also, specific examples of an iodonium cation (onium cation of I) include those represented by the following formula (3).

(2)

In the above formula (2), $R^{10}$, $R^{11}$ and $R^{12}$ each independently represent a linear or branched alkyl group having 1 to 10 carbon atoms, or an aromatic hydrocarbon group having 6 to 18 carbon atoms, wherein a part or all of hydrogen atoms included in the alkyl group and the aromatic hydrocarbon group represented by $R^{10}$, $R^{11}$ and $R^{12}$ are not substituted or substituted, or two of $R^{10}$, $R^{11}$ and $R^{12}$ optionally bond to one another to taken together represent a cyclic structure together with the sulfur atom to which the two of $R^{10}$, $R^{11}$ and $R^{12}$ bond.

(3)

In the above formula (3), $R^{13}$ and $R^{14}$ each independently represent a linear or branched alkyl group having 1 to 10 carbon atoms, or an aromatic hydrocarbon group having 6 to 18 carbon atoms, wherein a part or all of hydrogen atoms included in the alkyl group and the aromatic hydrocarbon group represented by $R^{13}$ and $R^{14}$ are not substituted or substituted, or $R^{13}$ and $R^{14}$ optionally bond to one another to taken together represent a cyclic structure together with the iodine atom to which $R^{13}$ and $R^{14}$ bond.

Examples of the linear or branched alkyl group having 1 to 10 carbon atoms represented by $R^{10}$ to $R^{12}$ include a methyl group, an ethyl group, a n-propyl group, an i-propyl group, a n-butyl group, a t-butyl group, a n-pentyl group, an i-pentyl group, a n-hexyl group, an i-hexyl group, a n-heptyl group, a n-octyl group, an i-octyl group, a n-nonyl group, a n-decyl group, a 2-ethylhexyl group, and the like.

A substituent which may be included in the alkyl group is exemplified by a halogen atom such as fluorine, chlorine, bromine or iodine, a hydroxyl group, a cyano group, a thiol group, an alkylthio group, an organic group such as an aromatic hydrocarbon group, an alkenyl group, an alkylcarboxyl group, an acyl group, an alkyl group that includes a hetero atom (for example, a halogen atom, an oxygen atom, a nitrogen atom, a sulfur atom, a phosphorus atom, a silicon atom, etc.), an alicyclic hydrocarbon group, and the like. Furthermore, a keto group derived from a hydrocarbon group by substituting two hydrogen atoms on single carbon by one oxygen atom may be exemplified. The number of the substituent is not limited within a range that provides a structurally acceptable substituted alkyl group.

Examples of the aromatic hydrocarbon group having 6 to 18 carbon atoms represented by $R^{10}$ to $R^{12}$ include a phenyl group, a 1-naphthyl group, a 2-naphthyl group, a 1-anthryl group, a 1-phenanthryl group, and the like.

Also, a substituent which may be included in the aromatic hydrocarbon group is exemplified by substituents similar to those exemplified as the substituent which may be included in the alkyl group.

Among the onium cations represented by the above formula (2), an onium cation represented by the following formula (2-1) or (2-2) is preferred.

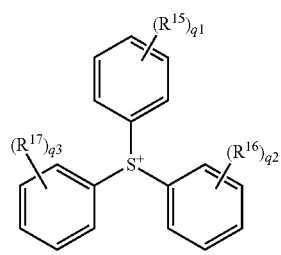

(2-1)

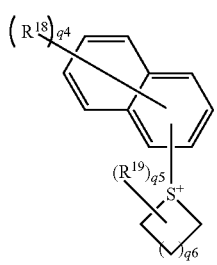

(2-2)

In the above formula (2-1), $R^{15}$ to $R^{17}$ each independently represent a hydrogen atom, a linear or branched alkyl group having 1 to 12 carbon atoms, an aromatic hydrocarbon group having 6 to 12 carbon atoms, $OSO_2$—$R^{20}$ or —$SO_2$—$R^{21}$, wherein $R^{20}$ and $R^{21}$ each independently represent a linear or branched alkyl group having 1 to 12 carbon atoms, an alicyclic hydrocarbon group having 5 to 25 carbon atoms, or an aromatic hydrocarbon group having 6 to 12 carbon atoms, and wherein a part or all of hydrogen atoms included in the alkyl group, the alicyclic hydrocarbon group and the aromatic hydrocarbon group represented by $R^{20}$ and $R^{21}$ are not substituted or substituted, or two or more of $R^{15}$ to $R^{17}$ optionally bond to one another to taken together represent a ring, wherein, in case where $R^{15}$ to $R^{17}$ are each present in a plurality of number, each of $R^{15}$s to $R^{17}$s may be identical or different, and wherein a part or all of hydrogen atoms included in the alkyl group and the aromatic hydrocarbon group represented by $R^{15}$ to $R^{17}$ are not substituted or substituted; and q1 to q3 are each independently an integer of 0 to 5.

In the above formula (2-2), $R^{18}$ represents a hydrogen atom, a linear or branched alkyl group having 1 to 8 carbon atoms, or an aromatic hydrocarbon group having 6 to 8 carbon atoms, wherein a part or all of hydrogen atoms included in the alkyl group and the aromatic hydrocarbon group represented by $R^{18}$ are not substituted or substituted, wherein, in a case where $R^{18}$ is present in a plurality of number, each of $R^{18}$s may be identical or different, and the plurality of $R^{18}$s optionally bond to one another to taken together represent a ring; $R^{19}$ represents a hydrogen atom, a linear or branched alkyl group having 1 to 7 carbon atoms, or an aromatic hydrocarbon group having 6 to 7 carbon atoms, wherein a part or all of hydrogen atoms included in the alkyl group and the aromatic hydrocarbon group represented by $R^{19}$ are not substituted or substituted, wherein, in a case where $R^{18}$ is present in a plurality of number, each of $R^{18}$s may be identical or different, and the plurality of $R^{18}$s optionally bond to one another to taken together represent a ring; q4 is an integer of 0 to 7; q5 is an integer of 0 to 6; and q6 is an integer of 0 to 3.

Examples of the linear or branched alkyl group having 1 to 12 carbon atoms represented by $R^{15}$ to $R^{17}$ include a methyl group, an ethyl group, a n-propyl group, an i-propyl group, a n-butyl group, a t-butyl group, a n-pentyl group, an i-pentyl group, a n-hexyl group, an i-hexyl group, a n-heptyl group, a n-octyl group, an i-octyl group, a n-nonyl group, a n-decyl group, a 2-ethylhexyl group, and the like.

Also, a substituent which may be included in the alkyl group represented by $R^{15}$ to $R^{17}$ is exemplified by substituents similar to those exemplified as the substituent which may be included in the alkyl group represented by $R^{10}$ to $R^{12}$.

Examples of the aromatic hydrocarbon group having 6 to 12 carbon atoms represented by $R^{15}$ to $R^{17}$ include a phenyl group, a naphthyl group, and the like.

Examples of the linear or branched alkyl group having 1 to 12 carbon atoms represented by $R^{20}$ and $R^{21}$ include a methyl group, an ethyl group, a n-propyl group, an i-propyl group, a n-butyl group, a t-butyl group, a n-pentyl group, an i-pentyl group, a n-hexyl group, an i-hexyl group, a n-heptyl group, a n-octyl group, an i-octyl group, a n-nonyl group, a n-decyl group, a 2-ethylhexyl group, and the like.

Examples of the alicyclic hydrocarbon group having 5 to 25 carbon atoms represented by $R^{20}$ and $R^{21}$ include a cyclopentyl group, a cyclohexyl group, a cyclooctyl group, an adamantyl group, a norbornyl group, and the like.

Examples of the aromatic hydrocarbon group having 6 to 12 carbon atoms represented by $R^{20}$ and $R^{21}$ include a phenyl group, a naphthyl group, and the like.

Examples of the linear or branched alkyl group having 1 to 8 carbon atoms represented by $R^{18}$ include a methyl group, an ethyl group, a n-propyl group, an i-propyl group, a n-butyl group, a t-butyl group, a n-pentyl group, an i-pentyl group, a n-hexyl group, an i-hexyl group, a n-heptyl group, a n-octyl group, an i-octyl group, a 2-ethylhexyl group, and the like.

Examples of the aromatic hydrocarbon group having 6 to 8 carbon atoms represented by $R^{18}$ include a phenyl group, and the like.

Examples of the linear or branched alkyl group having 1 to 7 carbon atoms represented by $R^{19}$ include a methyl group, an ethyl group, a n-propyl group, an i-propyl group, a n-butyl group, a t-butyl group, a n-pentyl group, an i-pentyl group, a n-hexyl group, an i-hexyl group, a n-heptyl group, and the like.

Examples of the aromatic hydrocarbon group having 6 to 7 carbon atoms represented by $R^{19}$ include a phenyl group, and the like.

A substituent which may be included in the alkyl group and the aromatic hydrocarbon group exemplified in the above formulae (2-1) and (2-2) is exemplified by groups similar to those exemplified as the substituent which may be included in the alkyl group represented by $R^{10}$ to $R^{12}$ in the above formula (2), and the like.

Of the sulfonium cations represented by the above formulae (2-1) and (2-2), those represented by the following formulae (i-1) to (i-13) are preferred. Of these, sulfonium cations represented by the following formulae (i-1), (i-6) to (i-13) are more preferred.

(i-1)
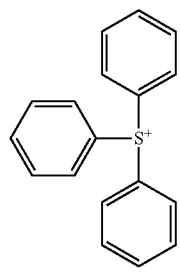

(i-2)
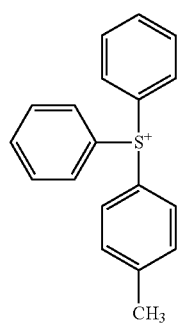

(i-3)
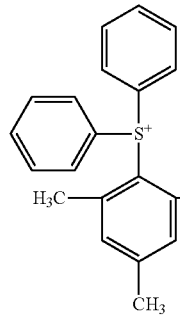

(i-4)
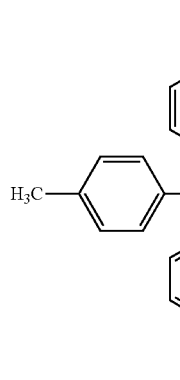

-continued (i-5)
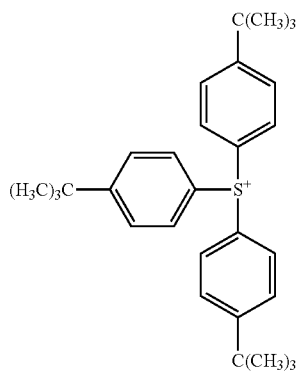

(i-6)
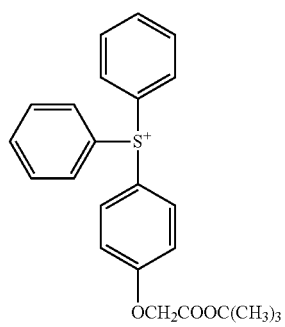

(i-7)
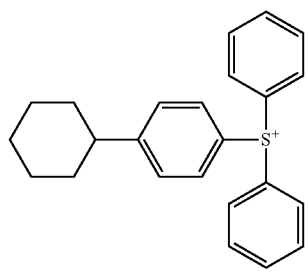

(i-8)
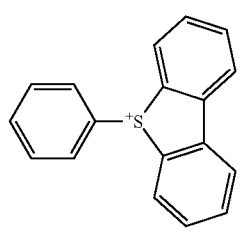

(i-9)
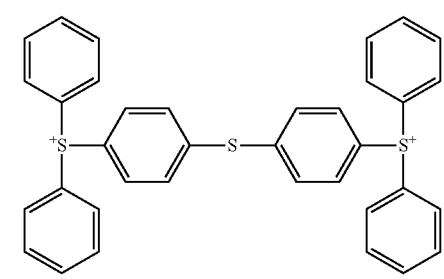

-continued

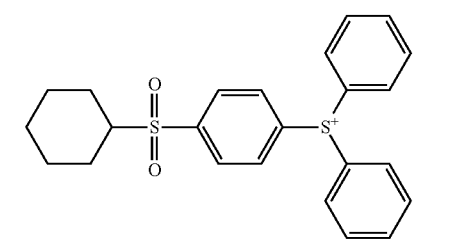
(i-10)

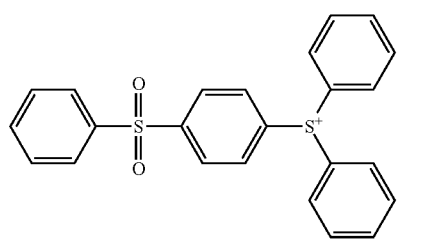
(i-11)

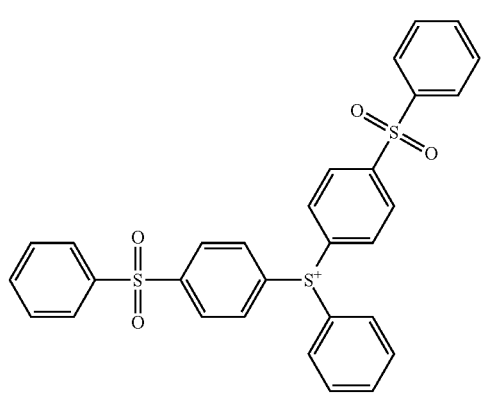
(i-12)

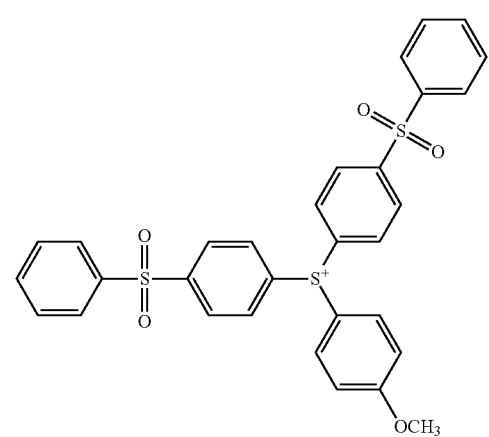
(i-13)

In the iodonium cation represented by the above formula (3), examples of the linear or branched alkyl group having 1 to 10 carbon atoms represented by $R^{13}$ and $R^{14}$ include a methyl group, an ethyl group, a n-propyl group, an i-propyl group, a n-butyl group, a t-butyl group, a n-pentyl group, an i-pentyl group, a n-hexyl group, an i-hexyl group, a n-heptyl group, a n-octyl group, an i-octyl group, a n-nonyl group, a n-decyl group, a 2-ethylhexyl group, and the like.

Examples of the aromatic hydrocarbon group having 6 to 18 carbon atoms represented by $R^{13}$ and $R^{14}$ include a phenyl group, a 1-naphthyl group, a 2-naphthyl group, a 1-anthryl group, a 1-phenanthryl group, and the like.

A substituent which may be included in the alkyl group and the aromatic hydrocarbon group exemplified in the above formula (3) is exemplified by substituents similar to those exemplified as the substituent which may be included in the alkyl group represented by $R^{10}$ to $R^{12}$ in the above formula (2).

Of the iodonium cations represented by the above formula (3), an onium cation represented by the following formula (3-1) is preferred.

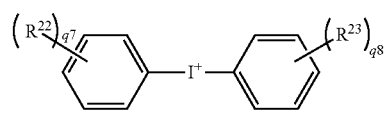
(3-1)

In the above formula (3-1), $R^{22}$ and $R^{23}$ each independently represent a hydrogen atom, a linear or branched alkyl group having 1 to 12 carbon atoms, or an aromatic hydrocarbon group having 6 to 12 carbon atoms; q7 and q8 are each independently an integer of 0 to 5, wherein, in a case where $R^{22}$ and $R^{23}$ is present in a plurality of number, a plurality of $R^{22}$ and $R^{23}$ are each identical or different, or two or more of $R^{22}$ and $R^{23}$ optionally bond to one another to taken together represent a ring.

Examples of the linear or branched alkyl group having 1 to 12 carbon atoms represented by $R^{22}$ and $R^{23}$ include a methyl group, an ethyl group, a n-propyl group, an i-propyl group, a n-butyl group, a 2-methylpropyl group, a 1-methylpropyl group, a t-butyl group, and the like.

Examples of the aromatic hydrocarbon group having 6 to 12 carbon atoms represented by $R^{22}$ and $R^{23}$ include a phenyl group, a naphthyl group, and the like.

The alkyl group and the aromatic hydrocarbon group in the above formula (3-1) exemplified above may have a substituent that is similar to the above-exemplified substituent which may be included in the alkyl group represented by $R^{10}$ to $R^{12}$ in the above formula (2).

Of the iodonium cations represented by the above formula (3-1), iodonium cations represented by the following formulae (ii-1) to (ii-3) are preferred. Of these, an iodonium cation represented by the formula (ii-1) or (ii-2) is more preferred.

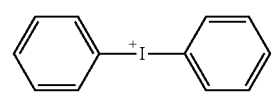
(ii-1)

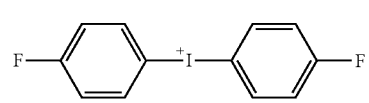
(ii-2)

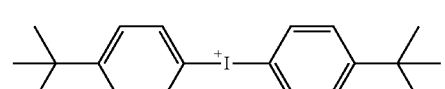
(ii-3)

The monovalent onium cation represented by $M^+$ in the compound (A) may be produced in accordance with a general method described in, for example, Advances in Polymer Science, Vol. 62, p. 1-48 (1984).

The compound (A) contained in the radiation-sensitive composition of the embodiment of the present invention is dissociates a monovalent onium cation ($M^+$) upon exposure or heating to generate an acid. Specifically, the compound (A)

generates a sulfonic acid represented by the following formula (1a), and preferably generates a sulfonic acid represented by the following formula (1-A-1a) or the following formula (1-B-1a).

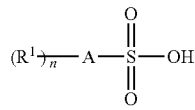

(1a)

In the formula (1a), $R^1$ and A are as defined in the above formula (1).

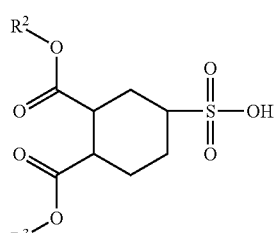

(1-A-1a)

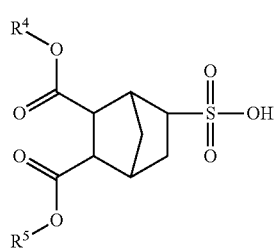

(1-B-1a)

In the formula (1-A-1a), $R^2$ and $R^3$ are as defined in the above formula (1-A-1). In the formula (1-B-1a), $R^4$ and $R^6$ are as defined in the above formula (1-B-1).

In the embodiment of the present invention, the compound (A) represented by the above formula (1) is preferably at least one compound selected from the group consisting of the compound represented by the above formula (1-A) and the compound represented by the above formula (1-B).

In the formulae (1-A) and (1-B), $R^1$ and $M^+$ are as defined in the above formula (1), wherein $M^+$ in the formula (1-A) and $M^+$ in the formula (1-B) are identical or different, and $R^1$ in the formula (1-A) and $R^1$ in the formula (1-B) are identical or different; $m_1$ is 0 or 1; and $m_2$ is an integer of 0 to 2.

$R^1$ in the above formula (1-A) and the above formula (1-B) may be exemplified by groups similar to the exemplified groups represented by $R^1$ in the above formula (1). In addition, $M^+$ in the above formula (1-A) and the above formula (1-B) may be exemplified by monovalent onium cations similar to the exemplified monovalent onium cations represented by $M^+$ in the above formula (1).

Also, it is particularly preferred that the compound represented by the above formula (1-A) is a compound represented by the following formula (1-A-1), and the compound represented by the above formula (1-B) is a compound represented by the following formula (1-B-1).

In the formula (1-A-1) and the formula (1-B-1), $R^2$, $R^3$, $R^4$ and $R^5$ each independently represent a linear or branched hydrocarbon group having 1 to 30 carbon atoms, an alicyclic hydrocarbon group having 3 to 30 carbon atoms, an aromatic hydrocarbon group having 6 to 30 carbon atoms, or a heterocyclic group having 4 to 30 carbon atoms, wherein the linear or branched hydrocarbon group may have an ester group, an amide group, a urethane group, a urea group, a carbonate group or a sulfide group between carbon atoms, and wherein a part or all of hydrogen atoms included in the hydrocarbon group, the alicyclic hydrocarbon group, the aromatic hydrocarbon group and the heterocyclic group represented by $R^2$, $R^3$, $R^4$ and $R^5$ are not substituted or substituted; and $M^+$ is as defined in the above formula (1).

Examples of the linear or branched hydrocarbon group having 1 to 30 carbon atoms represented by $R^2$, $R^3$, $R^4$ and $R^5$ include a methyl group, an ethyl group, a n-propyl group, an i-propyl group, a n-butyl group, a t-butyl group, a n-pentyl group, an i-pentyl group, a n-hexyl group, an i-hexyl group, a n-heptyl group, a n-octyl group, an i-octyl group, a n-nonyl group, a n-decyl group, a 2-ethylhexyl group, and a n-dodecyl group, and the like.

A substituent which may be included in the linear or branched hydrocarbon group having 1 to 30 carbon atoms is exemplified by groups similar to those exemplified as the substituent which may be included in the alkyl group represented by $R^{10}$ to $R^{12}$ in the above formula (2).

Examples of the linear or branched hydrocarbon group having 1 to 30 carbon atoms substituted with the substituent include a benzyl group, a methoxymethyl group, a methylthiomethyl group, an ethoxymethyl group, a phenoxymethyl group, a methoxycarbonylmethyl group, an ethoxycarbonylmethyl group, an acetylmethyl group, a fluoromethyl group, a trifluoromethyl group, a 2,2,2-trifluoroethyl group, a chloromethyl group, a trichloromethyl group, a 2-fluoropropyl group, a trifluoroacetylmethyl group, a trichloroacetylmethyl group, a pentafluorobenzoylmethyl group, an aminomethyl group, a cyclohexylaminomethyl group, a diphenylphosphinomethyl group, a trimethylsilylmethyl group, a 2-phenylethyl group, a 3-phenylpropyl group, a 2-aminoethyl group, a hydroxymethyl group, a hydroxyethyl group, a hydroxycarbonylmethyl group, a cyclopropylmethyl group, a cyclobutylmethyl group, a cyclopentylmethyl group, a cyclohexylmethyl group, a bornylmethyl group, a norbornylmethyl group, an adamantylmethyl group, a 3-hydroxymethyl-1-adamantanemethyl group, and the like.

Examples of the alicyclic hydrocarbon group having 3 to 30 carbon atoms represented by $R^2$, $R^3$, $R^4$ and $R^5$ include a cyclopropyl group, a cyclobutyl group, a cyclopentyl group, a cyclohexyl group, a bornyl group, a norbornyl group, an adamantyl group, a pinanyl group, thuiyl group, a caryle group, a camphonyl group, and the like.

A substituent which may be included in the alicyclic hydrocarbon group having 3 to 30 carbon atoms is exemplified by substituents similar to those exemplified as the substituent which may be included in the alkyl group represented by $R^{10}$ to $R^{12}$ in the above formula (2).

Examples of the alicyclic hydrocarbon group having 3 to 30 carbon atoms substituted with the substituent include a 4-fluorocyclohexyl group, a 4-hydroxycyclohexyl group, a 4-methoxycyclohexyl group, a 4-methoxycarbonylcyclohexyl group, a 3-hydroxy-1-adamantyl group, a 3-methoxycarbonyl-1-adamantyl group, a 3-hydroxycarbonyl-1-adamantyl group, and the like.

In addition, the phrase "having an ester group, an amide group, a urethane group, a urea group, a carbonate group or a sulfide group between carbon atoms" in the linear or branched hydrocarbon group means that a part of carbon-carbon bonds included in the hydrocarbon group is substituted with at least one selected from an ester group, an amide group, a urethane group, a urea group, a carbonate group and a sulfide group.

Examples of the aromatic hydrocarbon group having 6 to 30 carbon atoms represented by $R^2$, $R^3$, $R^4$ and $R^5$ include a phenyl group, a 1-naphthyl group, a 2-naphthyl group, a 1-anthryl group, a 1-phenanthryl group, and the like.

A substituent which may be included in the aromatic hydrocarbon group having 6 to 30 carbon atoms is exemplified by substituents similar to those exemplified as the substituent which may be included in the alkyl group represented by $R^{10}$ to $R^{12}$ in the above formula (2).

Examples of the aromatic hydrocarbon group having 6 to 30 carbon atoms substituted with the substituent include an o-hydroxyphenyl group, a m-hydroxyphenyl group, a p-hydroxyphenyl group, a 3,5-bis(hydroxy)phenyl group, an o-tolyl group, a m-tolyl group, a p-tolyl group, a p-methoxyphenyl group, a mesityl group, an o-cumenyl group, a 2,3-xylyl group, an o-fluorophenyl group, a m-fluorophenyl group, a p-fluorophenyl group, an o-trifluoromethylphenyl group, a m-trifluoromethylphenyl group, a p-trifluoromethylphenyl group, a 3,5-bis(trifluoromethyl)phenyl group, a p-bromophenyl group, a p-chlorophenyl group, a p-iodophenyl group, and the like.

Examples of the heterocyclic group having 4 to 30 carbon atoms represented by $R^2$, $R^3$, $R^4$ and $R^5$ include a furyl group, a thienyl group, a pyranyl group, a pyrrolyl group, a thianthrenyl group, pyrazolyl group, an isothiazolyl group, an isoxazolyl group, pyrazinyl group, pyrimidinyl group, pyridazinyl group, groups derived from a monocyclic or polycyclic lactone, and the like.

Examples of the monocyclic or polycyclic lactone include γ-butyrolactone, γ-valerolactone, angelicalactone, γ-hexanolactone, γ-heptanolactone, γ-octanolactone, γ-nonanolactone, 3-methyl-4-octanolide (whisky lactone), γ-decanolactone, γ-undecanolactone, γ-dodecanolactone, γ-jasmolactone (7-decenolactone), δ-hexanolactone, 4,6,6(4,4,6)-trimethyltetrahydropyran-2-one, δ-octanolactone, δ-nonanolactone, δ-decanolactone, δ-2-decenolactone, δ-undecanolactone, δ-dodecanolactone, δ-tridecanolactone, δ-tetradecanolactone, lactoscatone, ε-decanolactone, ε-dodecanolactone, cyclohexyl lactone, jasminelactone, cis-jasmolactone, methyl γ-decanolactone, lactones represented by the following formulae (R-1) and (R-2) (wherein a dotted line denotes a binding position), and the like.

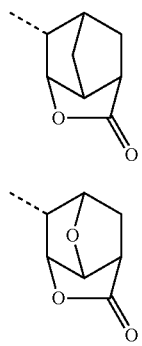

A substituent which may be included in the heterocyclic group is exemplified by substituents similar to those exemplified as the substituent which may be included in the alkyl group represented by $R^{10}$ to $R^{12}$ in the above formula (2).

Examples of the heterocyclic group having 4 to 30 carbon atoms substituted with the substituent include a 2-bromofuryl group, a 3-methoxythienyl group, and the like.

In addition, $M^+$ may be exemplified by monovalent onium cations similar to those exemplified as $M^+$ in the above formula (1).

Specific examples of the compound represented by the above formula (1-A-1) and the above formula (1-B-1) include compounds represented by the following formulae (1-1) to (1-10), and the like.

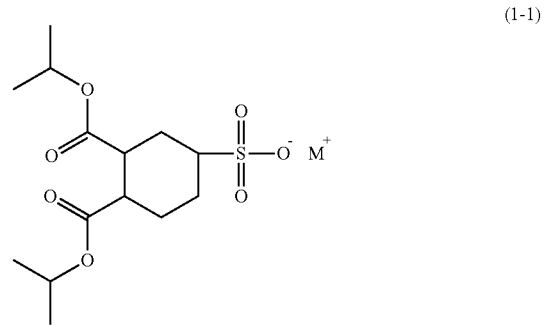

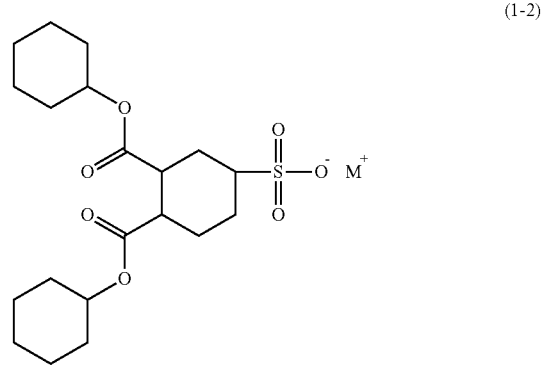

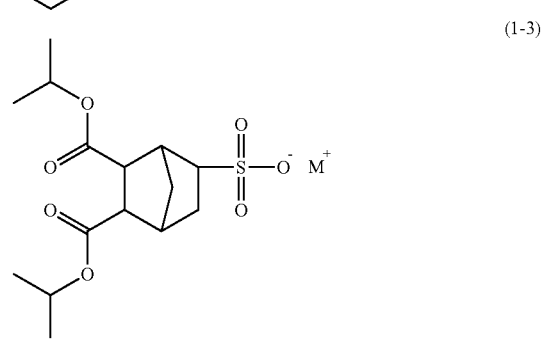

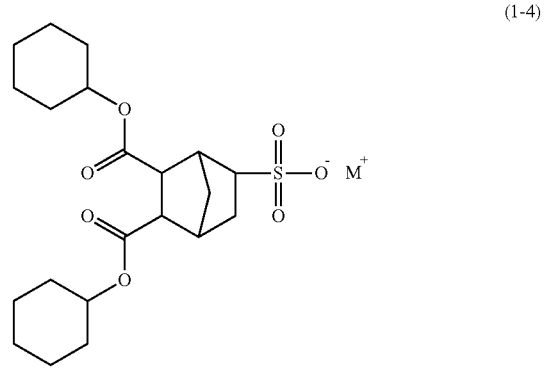

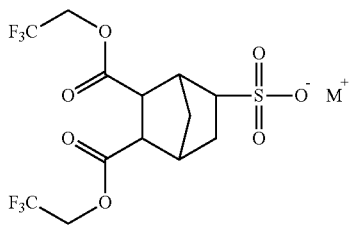
(1-5)

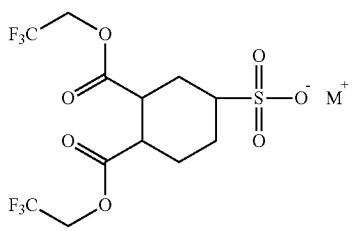
(1-6)

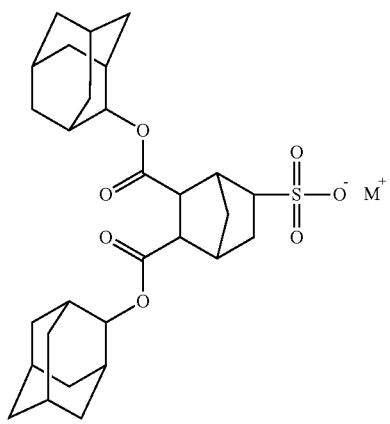
(1-7)

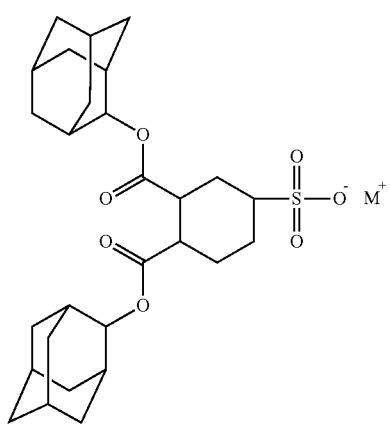
(1-8)

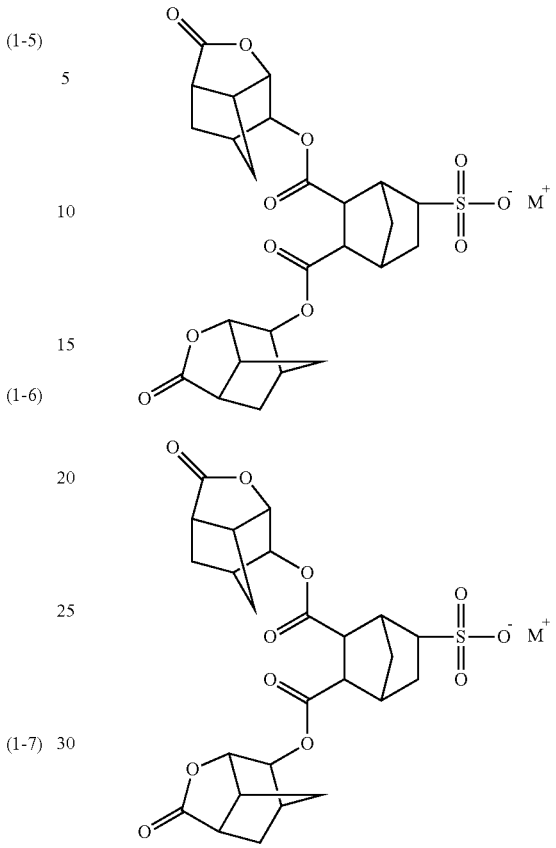
(1-9)

(1-10)

It is to be noted that in the radiation-sensitive composition of the embodiment of the present invention, other component, for example, a radiation-sensitive acid generating agent, which is described later, other than the compound (A) may be used in combination with the polymer (B), etc.

Moreover, a synthesis method of the compound (A) is not particularly limited, and for example, the compound (A) may be synthesized by allowing a compound represented by the following formula (X1) or (X2) to react with a halide of a desired onium cation ($M^+$) (for example, $M^+Br^-$) in an aqueous solution, as shown in each reaction formula below.

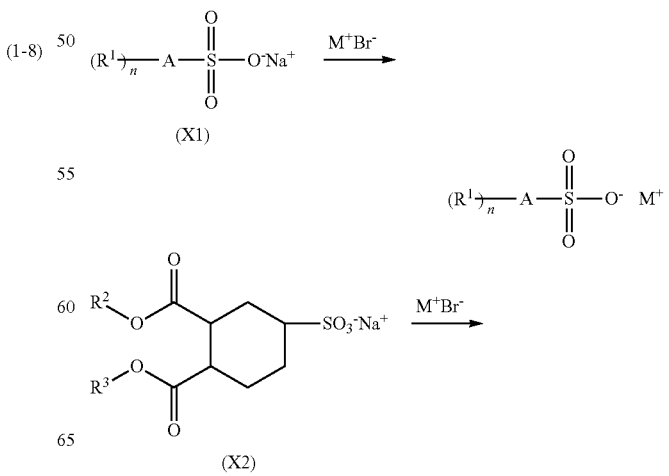

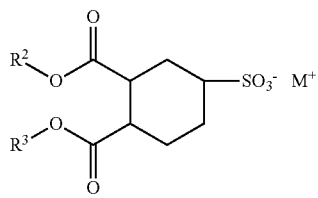

$R^1$, $R^2$, $R^3$ and $M^+$ in the above reaction formula are similarly defined to $R^1$, $R^2$, $R^3$ and $M^+$ in the above formulae (1) and (1-A-1).

It is to be noted that the radiation-sensitive composition of the embodiment of the present invention may contain either one type alone, or two or more types of the compound (A) described above.

The content of the compound (A) in the radiation-sensitive composition of the embodiment of the present invention is typically 0.1 to 50 parts by mass, preferably 1 to 40 parts by mass, and still more preferably 5 to 30 parts by mass with respect to 100 parts by mass of the polymer (B) described later. When the content of the compound (A) falls within the above-specified range, the radiation-sensitive composition achieves superior resolution.

Polymer (B)

The radiation-sensitive composition of the embodiment of the present invention contains the polymer (B) in addition to the compound (A). The polymer (B) has a structural unit that includes an acid-labile group (hereinafter, may be also referred to as "structural unit (III)"). Due to containing the polymer (B) having an acid-labile group in the radiation-sensitive composition, the acid-labile group is dissociated with the acid, as a catalyst, generated from the compound (A) upon exposure, leading to a change in a rate of dissolution in a developer solution, whereby a resist pattern can be formed.

It is preferred that the polymer (B) of the embodiment of the present invention further has the structural unit represented by the above formula (b-1) (hereinafter, may be referred to as "structural unit (I)"), the structural unit represented by the above formula (b-2) (hereinafter, may be referred to as "structural unit (II)"), or a combination thereof. In addition, other structural unit (IV) may be further included.

Structural Unit (I)

In the above formula (b-1), $R^6$ represents a hydrogen atom or a methyl group; $R^7$ represents a single bond, —CO—O—, or —CO—NH—; $R^8$ represents a linear or branched alkyl group having 1 to 12 carbon atoms, a linear or branched alkoxyl group having 1 to 12 carbon atoms, or an acyloxy group having 2 to 12 carbon atoms; R represents a group that includes a hydroxyl group or a hydroxyl group; p is 0 or 1; q and r are each independently an integer of 0 to 3, wherein, in a case where p is 0, the sum of q and r is no greater than 5, and in a case where $R^8$ is present in a plurality of number, the plurality of $R^8$s are identical or different.

In the formula (b-2), $R^9$ represents a hydrogen atom or a methyl group.

$R^7$ preferably represents —CO—O— in light of nanoedge roughness being superior.

Examples of the linear or branched alkyl group having 1 to 12 carbon atoms represented by $R^8$ include a methyl group, an ethyl group, a n-propyl group, an i-propyl group, a n-butyl group, a 2-methylpropyl group, a 1-methylpropyl group, a t-butyl group, and the like. Of these, a methyl group, an ethyl group, a n-butyl group and a t-butyl group are preferred in light of nanoedge roughness being superior.

Examples of the linear or branched alkoxyl group having 1 to 12 carbon atoms represented by $R^8$ include a methoxy group, an ethoxy group, a n-propoxy group, an i-propoxy group, a n-butoxy group, a 2-methylpropoxy group, a 1-methylpropoxy group, a t-butoxy group, and the like. Of these, a methoxy group and an ethoxy group are preferred in light of nanoedge roughness being superior.

Examples of the acyloxy group having 2 to 12 carbon atoms represented by $R^8$ include an acetoxy group, a propionyloxy group, a butyryloxy group, a pentylcarbonyloxy group, and the like. Of these, an acetoxy group is preferred in light of nanoedge roughness being superior.

The group that includes a hydroxyl group represented by R is exemplified by groups obtained by substituting a part or all of hydrogen atoms included in a linear or branched alkyl group having 1 to 12 carbon atoms, an alicyclic hydrocarbon group having 3 to 12 carbon atoms or the like by a hydroxyl group, and the like. It is to be noted that a part of hydrogen atoms included in the alkyl group and the alicyclic hydrocarbon group are not substituted or substituted by a group other than a hydroxyl group such as a fluorine atom.

The linear or branched alkyl group having 1 to 12 carbon atoms is exemplified by groups similar to those exemplified as the linear or branched alkyl group having 1 to 12 carbon atoms represented by $R^8$.

Examples of the alicyclic hydrocarbon group having 3 to 12 carbon atoms include a cyclopropyl group, a cyclobutyl group, a cyclopentyl group, a cyclohexyl group, a cyclooctyl group, a norbornyl group, and the like.

The group that includes a hydroxyl group represented by R is a is preferably a group obtained by substituting a part or all of hydrogen atoms included in a linear or branched alkyl group having 1 to 12 carbon atoms by a hydroxyl group, more preferably a group obtained by substituting a part or all of hydrogen atoms included in a linear or branched alkyl group having 1 to 5 carbon atoms by a hydroxyl group, and still more preferably a group obtained by substituting a part of hydrogen atoms included in a linear or branched alkyl group having 1 to 5 carbon atoms by a hydroxyl group and also substituting all the rest hydrogen atoms by a fluorine atom.

R preferably represents a hydroxyl group, or a group obtained by substituting a part of hydrogen atoms included in a linear or branched alkyl group having 1 to 5 carbon atoms by a hydroxyl group and further substituting all the rest hydrogen atoms by a fluorine atom.

In the above formula (b-1), p is preferably 0; q is more preferably 1 or 2; and r is preferably an integer of 0 to 2, and more preferably 0.

The structural unit represented by the above formula (b-1) may be exemplified by a structural unit represented by the following formulae, and the like. It is to be noted that either one type alone, or two or more types of the structural unit represented by the above formula (b-1) may be included in the polymer (B).

For example, in a case where $R^7$ represents a single bond and p is 0 in the above formula (b-1), structural units represented by the following formulae (b-1-1) to (b-1-4), and the like may be exemplified.

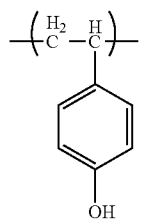
(b-1-1)

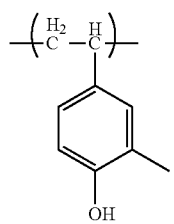
(b-1-2)

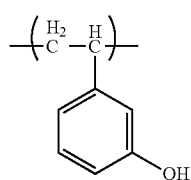
(b-1-3)

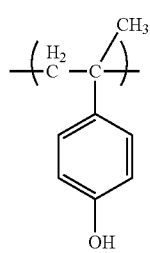
(b-1-4)

The structural units represented by the above formulae (b-1-1) to (b-1-4) may be obtained using a corresponding hydroxystyrene derivative as a monomer. Alternatively, a compound that gives the hydroxystyrene derivative through hydrolysis may be also used as a monomer to obtain the structural units.

Furthermore, in a case where $R^7$ represents —CO—O—, and p is 0 in the above formula (b-1), structural units represented by the following formulae (b-1-5) and (b-1-6), and the like may be exemplified.

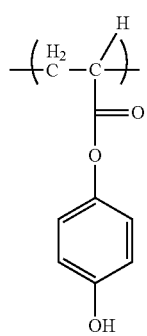
(b-1-5)

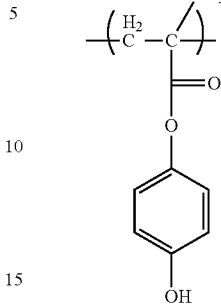
(b-1-6)

Examples of the monomer for use in producing the structural units presented above include 4-hydroxyphenyl acrylate, 4-hydroxyphenyl methacrylate, and the like.

Moreover, in a case where $R^7$ represents —CO—NH—, and p is 0 in the above formula (b-1), structural units represented by the following formulae (b-1-7) and (b-1-8), and the like may be exemplified.

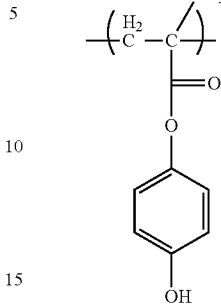
(b-1-7)

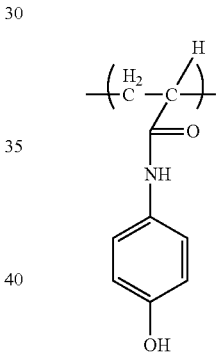
(b-1-8)

Examples of the monomer for use in producing the structural units presented above include N-(4-s hydroxyphenyl) acrylamide, N-(4-hydroxyphenyl)methacrylamide, and the like.

Additionally, in a case where $R^7$ represents —CO—O—, and p is 1 in the above formula (b-1), structural units represented by the following formulae (b-1-9) and (b-1-10), and the like may be exemplified.

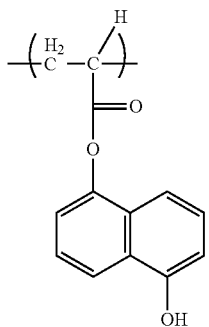
(b-1-9)

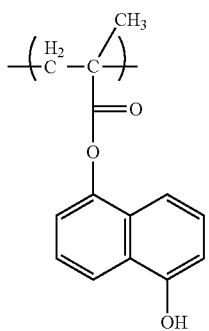
(b-1-10)

Examples of the monomer for use in producing the structural units presented above include 5-hydroxynaphthalen-1-yl methacrylate, 5-hydroxynaphthalen-1-yl acrylate, and the like.

In addition, in a case where R represents a group that includes a hydroxyl group in the above formula (b-1), structural units represented by the following formulae (b-1-11) and (b-1-12), and the like may be exemplified.

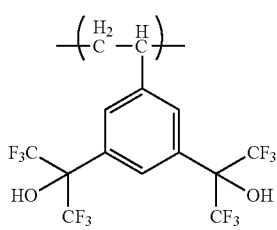
(b-1-11)

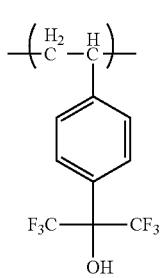
(b-1-12)

As the monomer for use in producing the structural units presented above, for example, a corresponding styrene derivative compound, a compound that gives the corresponding styrene derivative through hydrolysis, or the like may be used.

Structural Unit (II)

Due to including the structural unit (II) represented by the above formula (b-2) in the polymer (B), the radiation-sensitive composition can form a resist pattern that is more superior in nanoedge roughness.

The structural unit (II) is exemplified by structural units represented by the following formulae (b-2-1) and (b-2-2), and the like. It is to be noted that either one type alone, or two or more types of the structural unit (II) may be included in the polymer (B).

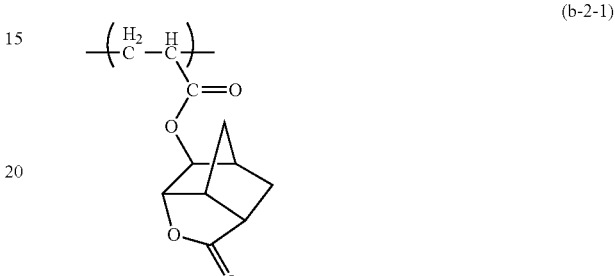
(b-2-1)

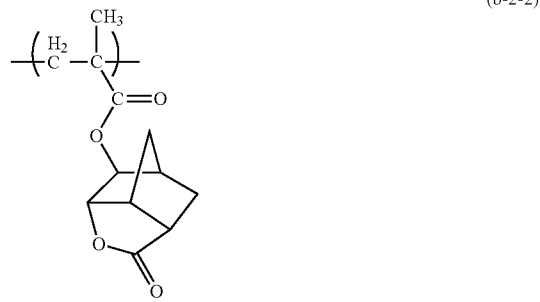
(b-2-2)

The monomer for use in producing the structural unit presented the above formula (b-2) is exemplified by compounds represented by the following formula (M-2-1) and the following formula (M-2-2), and the like.

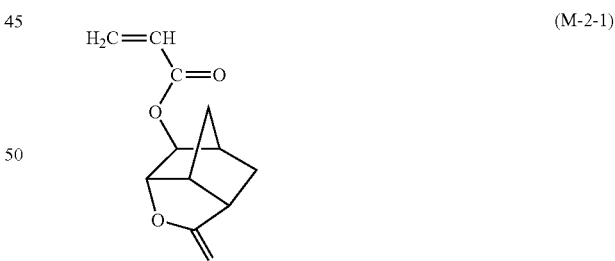
(M-2-1)

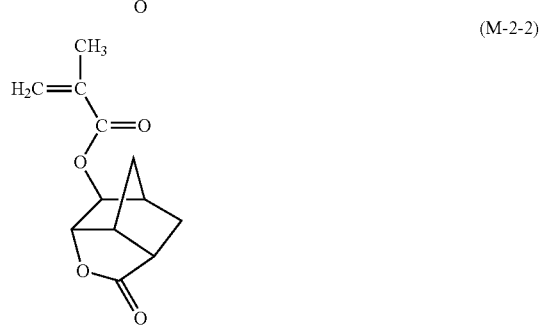
(M-2-2)

Structural Unit (III)

The polymer (B) has a structural unit (III) that includes an acid-labile group. The structural unit (III) is preferably at least one of a structural unit represented by the following formula (p-1) (hereinafter, may be also referred to as "structural unit (III-1)"), and a structural unit represented by the following formula (p-2) (hereinafter, may be also referred to as "structural unit (III-2)"). When the polymer (B) includes at least of the structural units (III-1) and (III-2) as the structural unit (III) in the radiation-sensitive composition, favorable sensitivity to radioactive rays can be attained.

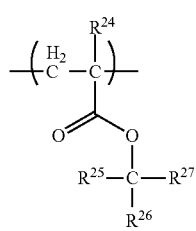
(p-1)

In the above formula (p-1), $R^{24}$ represents a hydrogen atom, a methyl group, a trifluoromethyl group or hydroxymethyl group; $R^{25}$ to $R^{27}$ each independently represent a linear or branched alkyl group having 1 to 4 carbon atoms, an aromatic hydrocarbon group having 6 to 22 carbon atoms, an alicyclic hydrocarbon group having 4 to 20 carbon atoms, or a group derived therefrom, or $R^{25}$ and $R^{26}$ optionally bond to one another to taken together represent a divalent alicyclic hydrocarbon group or a group derived therefrom together with the carbon atom to which $R^{25}$ and $R^{26}$ each bond.

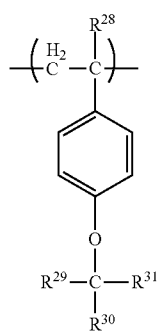
(p-2)

In the above formula (p-2), $R^{28}$ represents a hydrogen atom, a methyl group, a trifluoromethyl group or a hydroxymethyl group; $R^{29}$ to $R^{31}$ each independently represent an alicyclic hydrocarbon group having 4 to 20 carbon atoms, or a group derived therefrom, or $R^{29}$ and $R^{30}$ optionally bond to one another to taken together represent a divalent alicyclic hydrocarbon group or a group derived therefrom together with the carbon atom to which $R^{29}$ and $R^{30}$ each bond.

Examples of the alicyclic hydrocarbon group having 4 to 20 carbon atoms represented by $R^{25}$ to $R^{27}$ include a norbornyl group, a tricyclodecyl group, a tetracyclododecyl group, an adamantyl group, a cyclobutyl group, a cyclopentyl group, a cyclohexyl group, a cycloheptyl group, a cyclooctyl group, and the like.

In addition, the group derived from the alicyclic hydrocarbon group is exemplified by groups obtained by substituting a part or all of hydrogen atoms included in the alicyclic hydrocarbon group are substituted by, for example, a linear, branched, cyclic alkyl group having 1 to 4 carbon atoms such as a methyl group, an ethyl group, a n-propyl group, an i-propyl group, a n-butyl group, a 2-methylpropyl group, a 1-methylpropyl group or a t-butyl group, and the like.

The aromatic hydrocarbon group having 6 to 22 carbon atoms represented by $R^{25}$ to $R^{27}$ is exemplified by groups derived from structures represented by the following formulae (x-1) to (x-3), and the like. It is to be noted that in a case where $R^{25}$ to $R^{27}$ represent a naphthyl group derived from the following formula (x-2), a binding position to a carbon atom (i.e., carbon atom binding to an oxygen atom) in the above formula (p-1) may be either position 1 or 2. Alternatively, in a case where $R^{25}$ to $R^{27}$ represent an anthryl group derived from the following formula (x-3), a binding position to a carbon atom (i.e., carbon atom binding to an oxygen atom) in the above formula (p-1) may be any one of positions 1, 2 and 9.

A part or all of hydrogen atoms included in the aromatic hydrocarbon group are not substituted or substituted. Examples of the substituent include a methyl group, an ethyl group, a hydroxyl group, a carboxyl group, a halogen atom (e.g., a fluorine atom, a chlorine atom, a bromine atom, etc.), an alkoxyl group (e.g., a methoxy group, an ethoxy group, a propoxy group, a butoxy group, etc.), an alkyloxycarbonyl group, and the like.

(x-1)

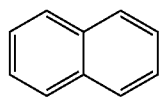
(x-2)

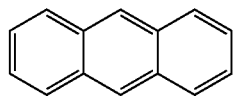
(x-3)

The divalent alicyclic hydrocarbon group taken together represented by $R^{25}$ and $R^{26}$ together with the carbon atom to which $R^{25}$ and $R^{26}$ each bond (i.e., carbon atom binding to an oxygen atom) is exemplified by a divalent alicyclic hydrocarbon group having 4 to 20 carbon atoms, and the like. Specific examples of such a divalent alicyclic hydrocarbon group include a norbornanediyl group, a tricyclodecanediyl group, a tetracyclododecanediyl group, an adamantanediyl group, a cyclopentanediyl group, a cyclohexanediyl group, and the like.

The group derived from the divalent alicyclic hydrocarbon group taken together represented by $R^{25}$ and $R^{26}$ by bonding to one another is exemplified by groups obtained by substituting the divalent alicyclic hydrocarbon group described above with at least one type or at least one of linear, branched or cyclic alkyl groups having 1 to 4 carbon atoms such as, for example, a methyl group, an ethyl group, a n-propyl group, an i-propyl group, a n-butyl group, a 2-methylpropyl group, a 1-methylpropyl group or a t-butyl group, and the like.

The structural unit (III-1) is preferably structural units represented by the following formulae (p-1-1) to (p-1-7), and more preferably a structural unit represented by the following formula (p-1-2), (p-1-3) or (p-1-4). When the polymer (B)

includes such a structural unit, the radiation-sensitive composition can form a resist pattern that is more superior in nanoedge roughness.

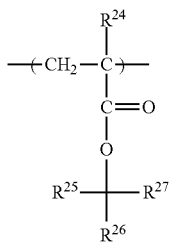
(p-1-1)

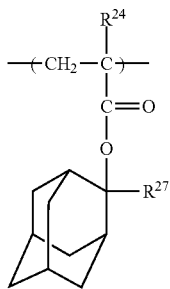
(p-1-2)

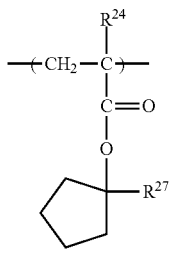
(p-1-3)

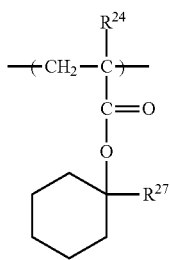
(p-1-4)

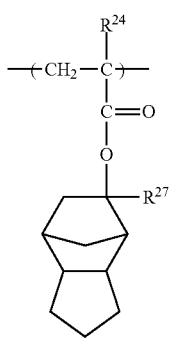
(p-1-5)

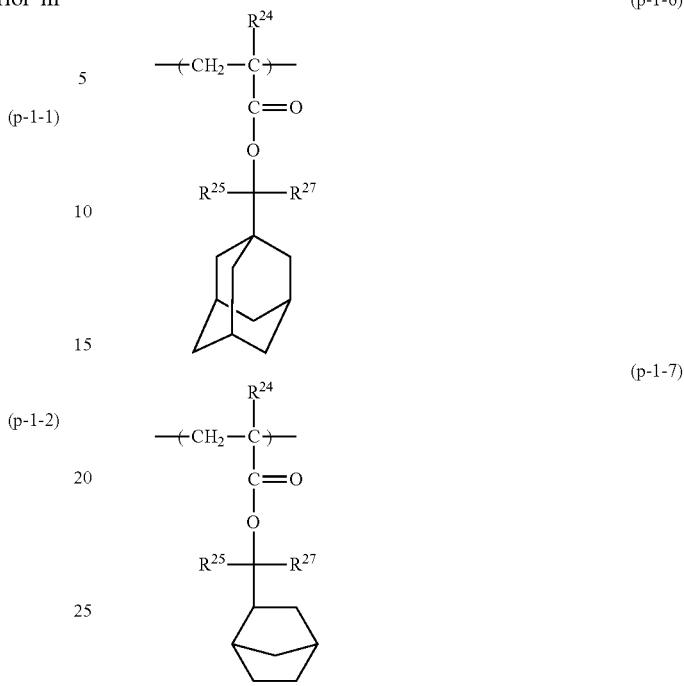

in the formulae (p-1-1) to (p-1-7), $R^{24}$ to $R^{27}$ are as defined in the above formula (p-1).

It is to be noted that either one type alone, or two or more types of the structural unit (III-1) may be included in the polymer (B).

In the above formula (p-2), the monovalent alicyclic hydrocarbon group having 4 to 20 carbon atoms or a group derived therefrom represented by $R^{29}$ to $R^{31}$, and the divalent alicyclic hydrocarbon group or a group derived therefrom taken together represented by $R^{29}$ and $R^{30}$ by bonding bond to one another together with the carbon atom to which $R^{29}$ and $R^{30}$ each bond, may be exemplified by groups similar to those exemplified as the monovalent alicyclic hydrocarbon group having 4 to 20 carbon atoms or a group derived therefrom represented by $R^{25}$ to $R^{27}$ in the above formula (p-1), and the divalent alicyclic hydrocarbon group or a group derived therefrom taken together represented by $R^{25}$ and $R^{26}$ by bonding to one another together with the carbon atom to which $R^{25}$ and $R^{26}$ each bond, respectively.

It is to be noted that either one type alone, or two or more types of the structural unit (III-2) may be included in the polymer (B).

Structural Unit (IV)

The polymer (B) may further include a structural unit (IV) derived from an non-acid labile compound as other structural unit in addition to the structural units (I), (II) and (III) described above. The non-acid labile compound as referred to herein means a compound that does not have a group dissociated by an action of an acid (acid-labile group). When the polymer (B) includes the structural unit (IV), the radiation-sensitive composition can form a resist pattern that is more superior in nanoedge roughness.

Examples of the non-acid labile compound that gives the structural unit (IV) include styrene, α-methylstyrene, 4-methylstyrene, 2-methylstyrene, 3-methylstyrene, isoboronyl acrylate, tricyclodecanyl (meth)acrylate, tetracyclododecenyl (meth)acrylate, and the like. Of these, styrene, α-methylstyrene, 4-methylstyrene, 2-methylstyrene, 3-methylstyrene and tricyclodecanyl acrylate are preferred. It is to be noted that either one type alone, or two or more types of the structural unit (IV) may be included in the polymer (B).

The proportion of the structural unit having an acid-labile group (III) included in the polymer (B) (particularly, proportion of the structural units (III-1) and (III-2) included in total) is preferably no less than 1 mol %, more preferably 10 to 70 mol %, and still more preferably 20 to 60 mol % with respect to 100 mol % of the total of entire structural units included in the polymer (B). When the proportion of the structural unit (III) included in the polymer (B) falls within the range specified above, the radiation-sensitive composition has superior sensitivity.

The total proportion of the structural units (I) and (II) included in the polymer (B) is preferably no less than 95 mol %, more preferably 1 to 95 mol %, still more preferably 10 to 95 mol %, and particularly preferably 40 to 80 mol % with respect to 100 mol % of the total of entire structural units included in the polymer (B). When the total proportion of the structural units (I) and (II) included in the polymer (B) falls within the range specified above, the radiation-sensitive composition can form a resist film that is more superior in nanoedge roughness.

The total proportion of the structural units (I), (II) and (III) included in the polymer (B) is preferably no less than 10 mol %, more preferably 40 to 100 mol %, and still more preferably 50 to 100 mol % with respect to 100 mol % of the total of entire structural units included in the polymer (B). When the total proportion of the structural units (I), (II) and (III) included in the polymer (B) falls within the range specified above, the radiation-sensitive composition can form a resist film that is more superior in nanoedge roughness.

The proportion of the structural unit (IV) included in the polymer (B) is preferably no greater than 60 mol %, and more preferably 0 to 50 mol % with respect to 100 mol % of the total of entire structural units included in the polymer (B). When the proportion of the structural unit (IV) included in the polymer (B) falls within the range specified above, the radiation-sensitive composition can form a resist film that is more superior in nanoedge roughness.

The synthesis method of the polymer (B) is not particularly limited, and the polymer (B) can be obtained by, for example, well-known radical polymerization or anion polymerization. Moreover, a phenol moiety or a naphthol moiety of a side chain in the above structural unit (I) can be obtained by subjecting the resulting polymer (B) to hydrolysis of an acetoxy group or the like in the presence of a base or an acid in an organic solvent.

The radical polymerization may be carried out by, for example, stirring and heating a monomer for producing at least one of the structural units (I) and (II) as a favorable component, a monomer for producing the structural unit (III), and a monomer for producing the structural unit (IV) which is added as needed in the presence of a radical polymerization initiator in an appropriate organic solvent in a nitrogen atmosphere.

Examples of the radical polymerization initiator include azo compounds such as 2,2'-azobisisobutyronitrile, 2,2'-azobis-(2,4-dimethylvaleronitrile), 2,2'-azobis-(4-methoxy-2,4-dimethylvaleronitrile), 2,2'-azobismethylbutyronitrile, 2,2'-azobiscyclohexanecarbonitrile, cyanomethylethylazoformamide, 2,2'-azobis(methyl 2,4-dimethylpropionate) and 2,2'-azobiscyanovaleric acid; organic peroxides such as benzoyl peroxide, lauroyl peroxide, 1,1'-bis-(t-butylperoxy)cyclohexane, 3,5,5-trimethylhexanoyl peroxide and t-butylperoxy-2-ethylhexanoate, as well as hydrogen peroxide, and the like.

Furthermore, a polymerize auxiliary such as 2,2,6,6-tetramethyl-1-piperidinyloxy, iodine, mercaptan or styrene dimer may be added in polymerization as needed.

The reaction temperature in the radical polymerization is not particularly limited, and may be appropriately set in accordance with the type of the initiator and the like, which may be for example, 50° C. to 200° C. Particularly, in the case in which the reaction is carried out using an azo initiator and/or a peroxide initiator, a temperature that leads to the half-life of the initiator of about 10 min to 30 hrs is preferred, and a temperature that leads to the half-life of the initiator of about 30 min to 10 hrs is more preferred.

In addition, the reaction time may vary depending on the type of the initiator and/or the reaction temperature, and a reaction time that leads to consumption of no less than 50% of the initiator is preferred, which is often about 0.5 hrs to 24 hrs.

The anion polymerization may be carried out by, for example, stirring and maintaining at a predetermined temperature a monomer that gives the structural unit (III), a monomer that gives at least one of the structural units (I) and (II), and a monomer that gives the structural unit (IV) as needed, in the presence of an anion polymerization initiator in an appropriate organic solvent in a nitrogen atmosphere.

Examples of the anion polymerization initiator include organic alkali metals such as n-butyllithium, s-butyllithium, t-butyllithium, ethyllithium, ethylsodium, 1,1-diphenyl hexyllithium and 1,1-diphenyl-3-methylpentyllithium.

The reaction temperature in the anion polymerization is not particularly limited, and may be appropriately set in accordance with the type of the initiator and the like. Particularly, in the case in which the reaction is carried out using alkyllithium as the initiator, the reaction temperature is preferably −100° C. to 50° C., and more preferably −78° C. to 30° C.

In addition, the reaction time may vary depending on the type of the initiator and/or the reaction temperature, and a reaction time that leads to consumption of no less than 50% of the initiator is preferred, which is often about 0.5 hrs to 24 hrs.

It is to be noted that in the synthesis of the polymer (B), carrying out a polymerization reaction by way of heating, and/or cation polymerization may be also employed, without using a polymerization initiator.

In the case in which a phenol moiety or a naphthol moiety of a side chain in the structural unit (I) described above is introduced by way of hydrolysis of a side chain of the polymer (B), examples of the acid which may be used in the hydrolysis reaction include: organic acids such as p-toluenesulfonic acid and a hydrate thereof, methanesulfonic acid, trifluoromethanesulfonic acid, malonic acid, oxalic acid and 1,1,1-fluoroacetic acid; inorganic acids such as sulfuric acid, hydrochloric acid, phosphoric acid and hydrobromic acid; pyridinium p-toluenesulfonate, ammonium p-toluenesulfonate, 4-methylpyridinium p-toluenesulfonate, and the like.

In the case in which a phenol moiety or a naphthol moiety of a side chain in the structural unit (I) described above is introduced by way of hydrolysis of a side chain of the polymer (B), examples of the base which may be used in the hydrolysis reaction include: inorganic bases such as potassium hydroxide, sodium hydroxide, sodium carbonate and potassium carbonate; organic bases such as triethylamine, N-methyl-2-pyrrolidone, piperidine and tetramethylammonium hydroxide, and the like.

Examples of the organic solvent which may be used for the polymerization and hydrolysis include: ketones such as acetone, methyl ethyl ketone and methyl amyl ketone; ethers such as diethyl ether and tetrahydrofuran (THF); alcohols such as methanol, ethanol and propanol; aliphatic hydrocarbons such as hexane, heptane and octane; aromatic hydrocarbons such as benzene, toluene and xylene; halogenated alkyls such as chloroform, bromoform, methylene chloride, methylene bromide and carbon tetrachloride; esters such as ethyl acetate, butyl acetate, ethyl lactate, propylene glycol monomethyl ether, propylene glycol monomethyl ether acetate and cellosolves; aprotic polar solvents such as dimethylformamide, dimethylsulfoxide and hexamethylphosphoroamide, and the like.

Of these, acetone, methyl amyl ketone, methyl ethyl ketone, tetrahydrofuran, methanol, ethanol, propanol, ethyl acetate, butyl acetate, ethyl lactate, propylene glycol monomethyl ether, and propylene glycol monomethyl ether acetate are preferred.

The weight average molecular weight in terms of the polystyrene equivalent (Mw) of the polymer (B) as determined by gel permeation chromatography (GPC) is preferably 3,000 to 100,000, more preferably 3,000 to 40,000, and still more preferably 3,000 to 25,000.

The ratio (Mw/Mn) of the Mw of the polymer (B) to the number average molecular weight in terms of the polystyrene equivalent (Mn) as determined by GPC is preferably 1 to 5, more preferably 1 to 3, and still more preferably 1 to 2.5.

It is to be noted that the radiation-sensitive composition may contain either one type alone, or two or more types of the polymer (B).

Solvent (C)

The radiation-sensitive composition contains the solvent (C) as a suitable component. The solvent (C) includes ethylene glycol monoalkyl ether acetate, propylene glycol monoalkyl ether acetate or a combination thereof in an amount of no less than 70% by mass of the entirety of the solvent (C). When the solvent (C) is used, the radiation-sensitive composition of the embodiment of the present invention can improve coating properties.

Examples of the ethylene glycol monoalkyl ether acetates include ethylene glycol monomethyl ether acetate, ethylene glycol monoethyl ether acetate, ethylene glycol mono-n-propyl ether acetate, ethylene glycol mono-n-butyl ether acetate, and the like.

Examples of the propylene glycol monoalkyl ether acetates include propylene glycol monomethyl ether acetate, propylene glycol monoethyl ether acetate, propylene glycol mono-n-propyl ether acetate, propylene glycol mono-n-butyl ether acetate, and the like.

The solvent (C) may contain other solvent except for the ethylene glycol monoalkyl ether acetate and the propylene glycol monoalkyl ether acetate.

Examples of the other solvent include: propylene glycol monoalkyl ethers such as propylene glycol monomethyl ether, propylene glycol monoethyl ether, propylene glycol mono-n-propyl ether and propylene glycol mono-n-butyl ether; propylene glycol dialkyl ethers such as propylene glycol dimethyl ether, propylene glycol diethyl ether, propylene glycol di-n-propyl ether and propylene glycol di-n-butyl ether.

Moreover, examples of the other solvent further include: lactic acid esters such as methyl lactate, ethyl lactate, n-propyl lactate and i-propyl lactate; formic acid esters such as n-amyl formate and i-amyl formate; acetic acid esters such as ethyl acetate, n-propyl acetate, i-propyl acetate, n-butyl acetate, i-butyl acetate, n-amyl acetate, i-amyl acetate, 3-methoxybutyl acetate and 3-methyl-3-methoxybutyl acetate; propionic acid esters such as i-propyl propionate, n-butyl propionate, i-butyl propionate and 3-methyl-3-methoxybutyl propionate; other esters such as ethyl hydroxyacetate, ethyl 2-hydroxy-2-methylpropionate, methyl 2-hydroxy-3-methylbutyrate, ethyl methoxyacetate, ethyl ethoxyacetate, methyl 3-methoxypropionate, ethyl 3-methoxypropionate, methyl 3-ethoxypropionate, ethyl 3-ethoxypropionate, 3-methyl-3-methoxybutylbutyrate, methyl acetoacetate, ethyl acetoacetate, methyl pyruvate and ethyl pyruvate; aromatic hydrocarbons such as toluene and xylene; ketones such as methyl ethyl ketone, 2-pentanone, 2-hexanone, 2-heptanone, 3-heptanone, 4-heptanone and cyclohexanone; amides such as N-methylformamide, N,N-dimethylformamide, N-methylacetamide, N,N-dimethylacetamide and N-methylpyrrolidone; lactones such as γ-butyrolactone, and the like. These other solvents may be used either one type alone, or in combination of two or more types thereof.

The amount of the solvent blended gives the total concentration of solid contents in the radiation-sensitive composition being preferably 1 to 70% by mass, more preferably 1 to 15% by mass, and still more preferably 1 to 10% by mass. When the amount blended falls within the range specified above, the radiation-sensitive composition is superior in coating properties and can form a resist film having a satisfactory thickness.

Other Optional Component

The radiation-sensitive composition may contain other optional component within the range not leading to impairment of within the range not leading to impairment of the desired effects of the present invention, in addition to the compound (A) and the polymer (B) contained as essential components, and the solvent (C) which may be contained as a favorable component. As the other optional component, various types of additives such as (D) an acid diffusion control agent, a radiation-sensitive acid generating agent other than the compound (A), a surfactant, a sensitizing agent and an aliphatic additive may be further contained.

Acid Diffusion Control Agent (D)

The acid diffusion control agent (D) has an effect of suppressing an unwanted chemical reaction in an unexposed region by controlling a phenomenon of diffusion of an acid, which is generated from the compound (A) upon exposure, in the resist film.

By containing such an acid diffusion control agent (D), the resultant radiation-sensitive composition has improved storage stability. In addition, the resolution of the resist film formed from the radiation-sensitive composition can be further enhanced, and inhibition of variation of the line width of the resist pattern is enabled that results from varying post exposure delay (PED) passed after completing the exposure until the heating treatment, and as a result, a radiation-sensitive composition that is extremely superior in the process stability can be obtained.

The acid diffusion control agent (D) is exemplified by a nitrogen-containing organic compound, a photosensitive basic compound, and the like.

The nitrogen-containing organic compound is exemplified by a compound represented by the following formula (4) (hereinafter, may be also referred to as "nitrogen-containing compound (i)"), compound having two nitrogen atoms in a single molecule (hereinafter, may be also referred to as "nitrogen-containing compound (ii)"), a polyamino compound and a polymer having three or more nitrogen atoms (hereinafter, may be also collectively referred to as "nitrogen-containing compound (iii)"), an amide group-containing compound, a urea compound, a nitrogen-containing heterocyclic compound, and the like.

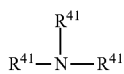
(4)

wherein, in the formula (4), each of $R^{41}$ independently represents a hydrogen atom, a linear, branched or cyclic alkyl group, an aromatic hydrocarbon group, or an aralkyl group, wherein a part or all of hydrogen atoms included in the alkyl group, aromatic hydrocarbon group and aralkyl group represented by $R^{41}$s are not substituted or substituted.

Examples of the nitrogen-containing compound (i) represented by the above formula (4) include mono(cyclo)alkylamines such as n-hexylamine, n-heptylamine, n-octylamine, n-nonylamine, n-decylamine and cyclohexylamine; di(cyclo)alkylamines such as di-n-butylamine, di-n-pentylamine, di-n-hexylamine, di-n-heptylamine, di-n-octylamine, di-n-nonylamine, di-n-decylamine, cyclohexylmethylamine and dicyclohexylamine; tri(cyclo)alkylamines such as triethylamine, tri-n-propylamine, tri-n-butylamine, tri-n-pentylamine, tri-n-hexylamine, tri-n-heptylamine, tri-n-octylamine, tri-n-nonylamine, tri-n-decylamine, cyclohexyldimethylamine, methyldicyclohexylamine and tricyclohexylamine; substituted alkylamines such as triethanolamine; aromatic amines such as aniline, N-methylaniline, N,N-dimethylaniline, 2-s methylaniline, 3-methylaniline, 4-methylaniline, 4-nitroaniline, diphenylamine, triphenylamine, naphthylamine, 2,4,6-tri-tert-butyl-N-methylaniline, N-phenyldiethanolamine, 2,6-diisopropylaniline, 2-(4-aminophenyl)-2-(3-hydroxyphenyl)propane and 2-(4-n aminophenyl)-2-(4-hydroxyphenyl)propane.

Examples of the nitrogen-containing compound (II) include ethylenediamine, N,N,N',N'-tetramethylethylenediamine, tetramethylenediamine, hexamethylenediamine, 4,4'-diaminodiphenylmethane, 4,4'-diaminodiphenyl ether, 4,4'-diaminobenzophenone, 4,4'-diaminodiphenylamine, 2,2-bis(4-aminophenyl)propane, 2-(3-aminophenyl)-2-(4-aminophenyl)propane, 1,4-bis[1-(4-aminophenyl)-1-methylethyl]benzene, 1,3-bis[1-(4-aminophenyl)-1-methylethyl]benzene, bis(2-dimethylaminoethyl)ether, bis(2-diethylaminoethyl)ether, 1-(2-hydroxyethyl)-2-imidazolidinone, 2-quinoxalinol, N,N,N',N'-tetrakis(2-hydroxypropyl)ethylenediamine, and the like.

Examples of the nitrogen-containing compound (iii) include polyethyleneimine, polyallylamine, polymers of 2-dimethylaminoethylacrylamide, and the like.

Examples of the amide group-containing compound include N-t-butoxycarbonyl group-containing amino compounds such as N-t-butoxycarbonyl di-n-octylamine, N-t-butoxycarbonyl di-n-nonylamine, N-t-butoxycarbonyl di-n-decylamine, N-t-butoxycarbonyl dicyclohexylamine, N-t-butoxycarbonyl-1-adamantylamine, N-t-butoxycarbonyl-2-adamantylamine, N-t-butoxycarbonyl-N-methyl-1-adamantylamine, (S)-(−)-1-(t-butoxycarbonyl)-2-n pyrrolidinemethanol, (R)-(+)-1-(t-butoxycarbonyl)-2-pyrrolidinemethanol, N-t-butoxycarbonyl-4-hydroxypiperidine, N-t-butoxycarbonylpyrrolidine, N-t-butoxycarbonylpiperazine, N,N-di-t-butoxycarbonyl-1-adamantylamine, N,N-di-t-butoxycarbonyl-N-methyl-1-adamantylamine, N-t-butoxycarbonyl-4,4'-diaminodiphenylmethane, N,N'-di-t-butoxycarbonyl hexamethylenediamine, N,N,N',N'-tetra-t-butoxycarbonyl hexamethylenediamine, N,N'-di-t-butoxycarbonyl-1,7-diaminoheptane, N,N'-di-t-butoxycarbonyl-1,8-diaminooctane, N,N'-di-t-butoxycarbonyl-1,9-diaminononane, N,N'-di-t-butoxycarbonyl-1,10-diaminodecane, N,N'-di-t-butoxycarbonyl-1,12-diaminododecane, N,N'-di-t-butoxycarbonyl-4,4'-diaminodiphenylmethane, N-t-butoxycarbonylbenzimidazole, N-t-butoxycarbonyl-2-methylbenzimidazole and N-t-butoxycarbonyl-2-phenylbenzimidazole, as well as formamide, N-methylformamide, N,N-dimethylformamide, acetamide, N-methylacetamide, N,N-dimethylacetamide, propionamide, benzamide, pyrrolidone, N-methylpyrrolidone, N-acetyl-1-adamantylamine, tris(2-hydroxyethyl) isocyanurate, and the like.

Examples of the urea compound include urea, methylurea, 1,1-dimethylurea, 1,3-dimethylurea, 1,1,3,3-tetramethylurea, 1,3-diphenylurea, tri-n-butylthiourea, and the like.

Examples of the nitrogen-containing heterocyclic compound include: imidazoles such as imidazole, 4-methylimidazole, 4-methyl-2-phenylimidazole, benzimidazole, 2-phenylbenzimidazole, 1-benzyl-2-methylimidazole and 1-benzyl-2-methyl-1H-imidazole; pyridines such as pyridine, 2-methylpyridine, 4-methylpyridine, 2-ethylpyridine, 4-ethylpyridine, 2-phenylpyridine, 4-phenylpyridine, 2-methyl-4-phenylpyridine, nicotine, nicotinic acid, nicotinic acid amide, quinoline, 4-hydroxyquinoline, 8-oxyquinoline, acridine and 2,2':6',2''-terpyridine; piperazines such as piperazine and 1-(2-hydroxyethyl)piperazine, as well as pyrazine, pyrazole, pyridazine, quinoxaline, purine, pyrrolidine, piperidine, piperidine ethanol, 3-piperidino-1,2-propanediol, morpholine, 4-methylmorpholine, 1-(4-morpholinyl)ethanol, 4-acetylmorpholine, 3-(N-morpholino)-1,2-propanediol, 1,4-dimethylpiperazine, 1,4-diazabicyclo[2.2.2]octane, and the like.

Although the photosensitive basic compound is not particularly limited as long as the properties described above are attained, for example, compounds represented by the following formulae (5-1) and (5-2), and the like may be exemplified.

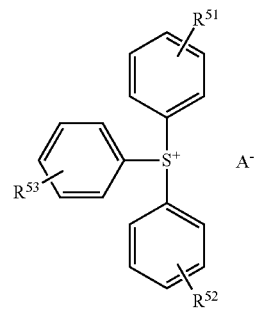
(5-1)

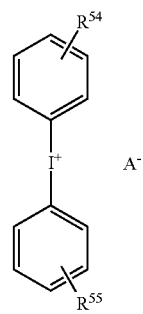
(5-2)

In the formula (5-1), $R^{51}$ to $R^{53}$ each independently represent a hydrogen atom, a halogen atom, an alkyl group having 1 to 10 carbon atoms, an alicyclic hydrocarbon group, an $—OSO_2—R^{56}$ group, or an $—SO_2—R^{57}$ group, wherein $R^{56}$ and $R^{57}$ each independently represent a an alkyl group having 1 to 10 carbon atoms, an alicyclic hydrocarbon group, or an aromatic hydrocarbon group, or two or more of $R^{51}$ to $R^{53}$ may bond to one another to taken together represent a cyclic structure; and $A^-$ represents $OH^-$, $R^{58}O^-$, or $R^{58}COO^-$, wherein $R^{58}$ represents a monovalent organic group.

In the formula (5-2), $R^{54}$ and $R^{55}$ each independently represent a hydrogen atom, a halogen atom, an alkyl group having 1 to 10 carbon atoms, or an alicyclic hydrocarbon group; and $A^-$ represents $OH^-$, $R^{59}O^-$, or $R^{59}COO^-$, wherein $R^{59}$ represents a monovalent organic group.

Wherein, a part or all of hydrogen atoms included in the alkyl group, the alicyclic hydrocarbon group, and the aromatic hydrocarbon group are not substituted or substituted.

Examples of the halogen atom represented by $R^{51}$ to $R^{53}$ in above formula (5-1) include a fluorine atom, a bromine atom, and the like.

Examples of the alkyl group having 1 to 10 carbon atoms represented by $R^{51}$ to $R^{57}$ in the above formulae (5-1) and (5-2) include a methyl group, an ethyl group, a n-propyl group, an i-propyl group, a n-butyl group, a 2-methylpropyl group, a 1-methylpropyl group, a t-butyl group, and the like.

Moreover, the alkyl group is unsubstituted or substituted with a substituent such as a hydroxyl group, a carboxyl group, a halogen atom (a fluorine atom, a bromine atom, etc.), an alkoxyl group (a methoxy group, an ethoxy group, a propoxy group, a butoxy group, a t-butoxy group, etc.), an alkyloxycarbonyl group (a t-butoxycarbonylmethyloxy group, etc.) or the like.

The alicyclic hydrocarbon group represented by $R^{51}$ to $R^{57}$ is exemplified by an alicyclic hydrocarbon group having 5 to 25 carbon atoms, and the like. Specifically, examples of the alicyclic hydrocarbon group include a cyclopentyl group, a cyclohexyl group, and the like. It is to be noted that the alicyclic hydrocarbon group is unsubstituted or substituted with a substituent such as a hydroxyl group, a carboxyl group, a halogen atom (a fluorine atom, a bromine atom, etc.), an alkoxyl group (a methoxy group, an ethoxy group, a propoxy group, a butoxy group, a t-butoxy group, etc.), an alkyloxycarbonyl group (a t-butoxycarbonylmethyloxy group, etc.).

The aromatic hydrocarbon group represented by $R^{56}$ and $R^{57}$ is exemplified by an aromatic hydrocarbon group having 6 to 12 carbon atoms, and the like. Specifically, examples of the aromatic hydrocarbon group include a phenyl group, a naphthyl group, and the like. It is to be noted that the aromatic hydrocarbon group is unsubstituted or substituted with a substituent such as an organic group that includes a halogen atom such as fluorine, chlorine, bromine or iodine, a hydroxyl group, a thiol group, an alkyl group, a hetero atom (for example, a halogen atom, oxygen atom, nitrogen atom, sulfur atom, phosphorus atom, silicon atom, etc.), and the like.

It is preferred that $R^{51}$ to $R^{55}$ in the above formulae (5-1) and (5-2) each represent a hydrogen atom, a methyl group, or a t-butyl group.

Examples of the monovalent organic group represented by $R^{58}$ and $R^{59}$ which may be included in $A^-$ in the above formulae (5-1) and (5-2) include an alkyl group, an aromatic hydrocarbon group, and the like. It is to be noted that a part or all of hydrogen atoms included in the alkyl group and the aromatic hydrocarbon group are not substituted or substituted.

$A^-$ preferably represents $OH^-$, $CH_3COO^-$, or any of compounds represented by the following formulae (6-1) to (6-5).

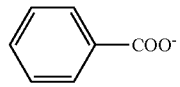

(6-1)

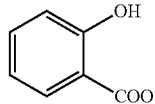

(6-2)

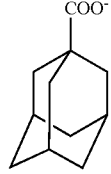

(6-3)

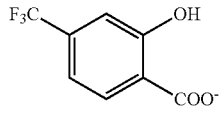

(6-4)

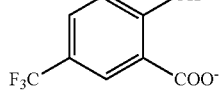

(6-5)

The photosensitive basic compound described above is specifically a triphenylsulfonium compound (the compound represented by the above formula (5-1)), and preferably a compound having an anion moiety ($A^-$) represented by $OH^-$, $CH_3COO^-$, or the above formula (6-2), (6-3) or (6-4). It is to be noted that the acid diffusion control agent (D) may be used either of one type alone, or in combination of two or more types thereof.

The content of the acid diffusion control agent (D) is preferably no greater than 15 parts by mass, more preferably 0.001 to 10 parts by mass, and still more preferably 0.005 to 5 parts by mass with respect to 100 parts by mass of the polymer (B). When the content of the acid diffusion control agent (D) falls within the range specified above, the radiation-sensitive composition achieves superior resolution.

Other Radiation-Sensitive Acid Generating Agent

The radiation-sensitive composition may further contain other radiation-sensitive acid generating agent (hereinafter, may be also referred to as "other acid generating agent) in addition to the compound (A). The other acid generating agent is exemplified by an onium salt compound, a sulfonic acid compound, and the like, excluding the compound (A).

The onium salt compound is exemplified by an iodonium salts, a sulfonium salt, a phosphonium salt, a diazonium salt, a pyridinium salt, and the like.

Specific examples of the onium salt compound include diphenyliodonium trifluoromethanesulfonate, diphenyliodonium nonafluoro-n-butanesulfonate, diphenyliodonium perfluoro-n-octanesulfonate, bis(4-t-butylphenyl)iodonium trifluoromethanesulfonate, bis(4-t-butylphenyl)iodonium nonafluoro-n-butanesulfonate, bis(4-t-butylphenyl)iodonium perfluoro-n-octanesulfonate, cyclohexyl 2-oxocyclohexylmethylsulfonium trifluoromethanesulfonate, dicyclohexyl 2-oxocyclohexylsulfonium trifluoromethanesulfonate, 2-oxocyclohexyldimethylsulfonium trifluoromethanesulfonate, bis(4-t-butylphenyl)iodonium nonafluorobutanesulfonate, bis(4-t-butylphenyl)iodonium trifluoromethanesulfonate, bis (4-t-butylphenyl)iodonium perfluorooctanesulfonate, bis(4-t-butylphenyl)iodonium p-toluenesulfonate, bis(4-t-butylphenyl)iodonium 10-camphorsulfonate, bis(4-t-butylphenyl)iodonium 4-trifluoromethylbenzenesulfonate, bis(4-t-butylphenyl)iodonium perfluorobenzenesulfonate, diphenyliodonium p-toluenesulfonate, diphenyliodonium benzenesulfonate, diphenyliodonium 10-camphorsulfonate, diphenyliodonium 4-trifluoromethylbenzenesulfonate, diphenyliodonium perfluorobenzenesulfonate, bis(p-fluorophenyl)iodonium trifluoromethanesulfonate, bis(p-fluorophenyl)iodonium nonafluoromethanesulfonate, bis(p-fluorophenyl)iodonium 10-camphorsulfonate, (p-fluorophenyl)(phenyl)iodonium trifluoromethanesulfonate, triphenylsulfonium nonafluorobutanesulfonate, triphenylsulfonium trifluoromethanesulfonate, triphenylsulfonium perfluorooctanesulfonate, triphenylsulfonium-2-bicyclo[2.2.1]hept-2-yl-1,1-difluoroethanesulfonate, triphenylsulfonium-2-bicyclo[2.2.1]hept-2-yl-1,1,2,2-tetrafluoroethanesulfonate, triphenylsulfonium p-toluenesulfonate, triphenylsulfonium benzenesulfonate, triphenylsulfonium 10-camphorsulfonate, triphenylsulfonium 4-trifluoromethylbenzenesulfonate, triphenylsulfonium perfluorobenzenesulfonate, 4-hydroxyphenyldiphenylsulfonium trifluoromethanesulfonate, tris(p-methoxyphenyl)sulfonium nonafluorobutanesulfonate, tris(p-methoxyphenyl)sulfonium trifluoromethanesulfonate, tris(p-methoxyphenyl)sulfonium perfluorooctanesulfonate, tris(p-methoxyphenyl)sulfonium p-toluenesulfonate, tris(p-methoxyphenyl)sulfonium benzenesulfonate, tris(p-methoxyphenyl)sulfonium 10-camphorsulfonate, tris(p-fluorophenyl)sulfonium trifluoromethanesulfonate, tris(p-fluorophenyl)sulfonium p-toluenesulfonate, (p-fluorophenyl)diphenylsulfonium trifluoromethanesulfonate, 4-butoxy-1-naphthyltetrahydrothiophenium nonafluorobutanesulfonate, and 4-butoxy-1-naphthyltetrahydrothiophenium-2-bicyclo[2.2.1]hept-2-yl-1,1,2,2-tetrafluoroethanesulfonate, and the like.

The sulfonic acid compound is exemplified by an alkylsulfonic acid ester, alkylsulfonic acid imide, haloalkylsulfonic acid ester, arylsulfonic acid ester, and imino sulfonate, and the like. Specifically, examples of the sulfonic acid compound include benzointosylate, tris(trifluoromethanesulfonate) of pyrogallol, nitrobenzyl-9,10-diethoxyanthracene-2-sulfonate, trifluoromethanesulfonyl bicyclo[2.2.1]hept-5-ene-2,3-dicarbodiimide, nonafluoro-n-butanesulfonylbicyclo[2.2.1]hept-5-ene-2,3-dicarbodiimide, perfluoro-n-octanesulfonylbicyclo[2.2.1]hept-5-ene-2,3-dicarbodiimide, N-hydroxysuccinimidetrifluoromethanesulfonate, N-hydroxysuccinimidenonafluoro-n-butanesulfonate, N-hydroxysuccinimideperfluoro-n-octanesulfonate, 1,8-naphthalenedicarboxylic acid imidetrifluoromethanesulfonate, 1,8-naphthalenedicarboxylic acid imidenonafluoro-n-butanesulfonate, and 1,8-naphthalenedicarboxylic acid imideperfluoro-n-octanesulfonate, and the like.

Of these other acid generating agents, diphenyliodonium trifluoromethanesulfonate, diphenyliodonium nonafluoro-n-butanesulfonate, diphenyliodonium perfluoro-n-octanesulfonate, bis(4-t-butylphenyl)iodonium trifluoromethanesulfonate, bis(4-t-butylphenyl)iodonium nonafluoro-n-butanesulfonate, bis(4-t-butylphenyl)iodonium perfluoro-n-octanesulfonate, cyclohexyl 2-oxocyclohexylmethylsulfonium trifluoromethanesulfonate, dicyclohexyl 2-oxocyclohexylsulfonium trifluoromethanesulfonate, 2-oxocyclohexyl dimethylsulfonium trifluoromethanesulfonate, trifluoromethanesulfonyl bicyclo[2.2.1]hept-5-ene-2,3-dicarbodiimide, nonafluoro-n-butanesulfonylbicyclo[2.2.1]hept-5-ene-2,3-dicarbodiimide, perfluoro-n-octanesulfonylbicyclo[2.2.1]hept-5-ene-2,3-dicarbodiimide, N-hydroxysuccinimidetrifluoromethanesulfonate, N-hydroxysuccinimidenonafluoro-n-butanesulfonate, N-hydroxysuccinimideperfluoro-n-octanesulfonate, 1,8-naphthalenedicarboxylic acid imidetrifluoromethanesulfonate, triphenylsulfonium nonafluorobutanesulfonate, triphenylsulfonium trifluoromethanesulfonate, triphenylsulfonium-2-bicyclo[2.2.1]hept-2-yl-1,1-n difluoroethanesulfonate, triphenylsulfonium-2-bicyclo[2.2.1]hept-2-yl-1,1,2,2-tetrafluoroethanesulfonate, 4-butoxy-1-naphthyltetrahydrothiophenium nonafluorobutanesulfonate, and 4-butoxy-1-naphthyltetrahydrothiophenium-2-bicyclo[2.2.1]hept-2-yl-1,1,2,2-tetrafluoroethanesulfonate are preferred. It is to be noted that these other acid generating agents may be used either of one type alone, or in combination of two or more types thereof.

The amount of the other acid generating agent blended is preferably 0 to 80 parts by mass, and more preferably 0 to 50 parts by mass with respect to 100 parts by mass of the polymer (B), in light of securing the sensitivity and developability of the resist film formed from the radiation-sensitive composition. When the content of the other acid generating agent in the radiation-sensitive composition falls within the range specified above, the resolution of the radiation-sensitive composition can be further improved.

Surfactant

A surfactant is a component having an effect of improving coating properties, striation, developability, and the like.

Sensitizing Agent

A sensitizing agent absorbs energy of radioactive rays, and transfers the absorbed energy to the compound (A), thereby exhibiting an effect of increasing the amount of formation of the generated acid, and is thus effective in improving apparent sensitivity of the radiation-sensitive composition.

Alicyclic Additive

An alicyclic additive is a component having an effect of further improving dry-etching resistance, pattern configuration, adhesiveness to the substrate, and the like.

Furthermore, in addition to these additives, an alkali-soluble polymer, a low molecular alkali-solubility controlling agent having an acid-labile protecting group, a halation inhibitor, a storage stabilizing agent, a defoaming agent and the like may be also blended.

Preparation Method of Radiation-Sensitive Composition

The radiation-sensitive composition may be prepared by homogenously dissolving in the solvent (C) such that the total solid content concentration falls within the above range, the compound (A) and the polymer (B), as well as the acid diffusion control agent (D) and the additives such as the other acid generating agent and the surfactant which are added as needed. It is to be noted that after preparing in this manner, the radiation-sensitive composition is preferably filtered through a filter having a pore size of about 0.2 μm, for example.

Resist Pattern-Forming Method

The radiation-sensitive composition is suitably used for forming a resist pattern. Specifically, for example, in a chemically amplified positive type resist film constituted with the radiation-sensitive composition, an action of an acid generated from the compound (A) upon exposure allows the acid-labile group in the polymer (B) to be dissociated, whereby the polymer (B) turns to be soluble in an alkali. In other words, alkali-soluble sites are generated on the resist film. The alkali-soluble site is a light-exposed site of the resist, and the light-exposed site can be dissolved in the alkaline developer solution, and removed. Accordingly, a positive type resist pattern having a desired shape can be formed. Hereinafter, the resist pattern-forming method will be described in detail.

In order to form a resist pattern using the radiation-sensitive composition of the embodiment of the present invention, a resist film is first provided by the radiation-sensitive composition of the embodiment of the present invention. As the radiation-sensitive composition, for example, one obtained by filtering through a filter having a pore size of about 0.2 μm after adjusting the total concentration of solid contents as described above may be used. The resist film is provided by coating the radiation-sensitive composition by an appropriate coating means such as spin-coating, cast coating or roll coating on a substrate such as, for example, a silicon wafer or a wafer coated with aluminum. Thereafter, a heating treatment (PB) may be optionally carried out beforehand at a temperature of about 70° C. to 160° C.

Next, the resist film is exposed such that a predetermined resist pattern is formed. The radioactive ray which may be employed for the exposure is exemplified by (extreme) far ultraviolet rays such as a KrF excimer laser (wavelength: 248 nm), an ArF excimer laser (wavelength: 193 nm) and an EUV (extreme ultraviolet ray; wavelength: 13.5 nm, etc.), X-rays such as a synchrotron radioactive ray, charged particle rays such as an electron beam, and the like. Also, conditions of the exposure such as an exposure dose may be appropriately determined in accordance with the blend composition of the radiation-sensitive resin composition, as well as the type of the additives, and the like. It is to be noted that the exposure may be also executed by liquid immersion lithography.

After the exposure, a heating treatment (PEB) is preferably carried out. The PEB enables dissociation of the acid-labile group of the polymer (B) to smoothly proceed. Heating conditions of PEB may be appropriately determined depending on blend composition of the radiation-sensitive composition, and involves preferably 30° C. to 200° C. and more preferably 50° C. to 170° C.

In the embodiment of the present invention, in order to maximize the potential capability of the radiation-sensitive composition, an organic or inorganic antireflective film may be also provided on the substrate employed as disclosed in, for example, Japanese Examined Patent Application, Publication No. H6-12452 (Japanese Unexamined Patent Application, Publication No. S59-93448) and the like. Moreover, in order to prevent influences from basic impurities, etc., included in the environment atmosphere, a protective film may be provided on the resist film as disclosed in, for example, Japanese Unexamined Patent Application, Publication No. H5-188598 and the like. It is to be noted that these techniques may be used in combination.

Subsequently, a predetermined resist pattern is formed by subjecting the exposed resist film to development. Examples of preferred developer solution for use in the development include aqueous alkaline solutions prepared by dissolving at least one alkaline compound such as sodium hydroxide, potassium hydroxide, sodium carbonate, sodium silicate, sodium metasilicate, ammonia, ethylamine, n-propylamine, diethylamine, di-n-propylamine, triethylamine, methyldiethylamine, ethyldimethylamine, triethanolamine, tetramethylammonium hydroxide, pyrrole, piperidine, choline, 1,8-diazabicyclo-[5.4.0]-7-undecene or 1,5-diazabicyclo-[4.3.0]-5-nonene.

The concentration of the aqueous alkaline solution is preferably no greater than 10% by mass. When the concentration of the aqueous alkaline solution is greater than 10% by mass, sites unexposed with light may be also dissolved in the developing solution. In addition, the developing solution has a pH of preferably 8 to 14 and more preferably has 9 to 14.

To the developer solution consisting of the aqueous alkaline solution may be also added, for example, an organic solvent. Examples of the organic solvent include ketones such as acetone, methyl ethyl ketone, methyl i-butyl ketone, cyclopentanone, cyclohexanone, 3-methylcyclopentanone and 2,6-dimethyl cyclohexanone; alcohols such as methanol, ethanol, n-propyl alcohol, i-propyl alcohol, n-butyl alcohol, t-butyl alcohol, cyclopentanol, cyclohexanol, 1,4-hexanediol and 1,4-hexanedimethylol; ethers such as tetrahydrofuran and dioxane; esters such as ethyl acetate, n-butyl acetate and i-amyl acetate; aromatic hydrocarbons such as toluene and xylene, as well as phenol, acetonyl acetone, dimethylformamide, and the like. These organic solvent may be used either of one type alone, or in combination of two or more types thereof.

It is to be noted that after the development carried out with the developer solution consisting of the aqueous alkaline solution, the resist film may be washed with water and dried.

Compound

The compound of the embodiment of the present invention is represented by the above formula (1). The compound is represented by preferably the above formula (1-A) or (1-B), and more preferably the above formula (1-A-1) or (1-B-1). The compound is highly soluble in solvents, and can be suitably used as the compound (A) in the radiation-sensitive composition. When the compound is used as the acid generating agent in a radiation-sensitive composition, due to the compound being bulky and highly polar, a diffusion length of the acid generated upon exposure can be controlled to be appropriately short, whereby smoothness of the surface of a resist film after resolution and pattern formation can be improved. In addition, since the compound has a high boiling point, it is less likely to be volatilized during a pattern formation step, and thus formation of a favorable pattern is enabled. It is to be noted explanations of the compound (A) used as an essential component of the radiation-sensitive composition may be applied as is to the compound.

EXAMPLES

Hereinafter, the embodiments of the present invention will be more specifically explained by way of Examples. However, the present invention is not in any way limited to these Examples. It is to be noted that although EB (electron beam) and ArF were used for exposure of a resist film in the Examples, similar basic resist characteristics are exhibited also in the case in which a radioactive ray having a short wavelength such as EUV is used, and it is also known that there is a correlation between the basic resist characteristics of EB or ArF, and those of the short wave length radioactive ray.

Synthesis of Radiation-Sensitive Acid Generating Agent (Compound (A))

Example 1

Synthesis of (A-1)

In an egg-plant shaped flask, 16.4 g of (I-1) a compound represented by the following formula (I-1), 30.0 g of (I-2) a compound represented by the following formula (I-2), 1.7 g of paratoluenesulfonic acid and 200 g of toluene were mixed, and allowed them to react for 8 hrs under reflux with toluene. After completion of the reaction, toluene was distilled in vacuo, and methylene chloride was added thereto, followed by washing of the organic layer with a 3 wt % aqueous NaHCO$_3$ solution three times and then with water three times. Thereafter, methylene chloride was distilled in vacuo, and silica gel column chromatography was carried out using a mixed solvent of ethyl acetate/n-hexane=1/1 (volume ratio) as a developing solvent to obtain an intended compound (I-3) represented by the following formula (I-3) (yield: 60%).

In an egg-plant shaped flask, 15.0 g of the compound (I-3), 13.5 g of NaHSO$_3$, 50 g of water and 50 g of methanol were mixed, and allowed them to react for 8 hrs. After completion of the reaction, water/methanol was distilled in vacuo. The solid thus obtained was dissolved in 100 g of water and thereto was added 50 g of tetrahydrofuran. The mixture was stirred for 30 min at room temperature and left to stand for 30 min. Only the upper layer among two layers separated was recovered, and the solvent in the upper layer was distilled in vacuo to obtain a compound (I-4) represented by the following formula (I-4) (yield: 70%).

In an egg-plant shaped flask, 5.0 g of the compound (I-4), 3.3 g of a compound (I-5) represented by the following formula (I-5), 100 g of methylene chloride and 100 g of water were mixed, and the mixture was stirred for 10 hrs at room temperature. After completion of the reaction, a methylene chloride layer was recovered, and washed with 500 g of water four times. Thereafter, the methylene chloride layer was recovered, and methylene chloride was distilled in vacuo to obtain an intended compound (A-1) represented by the following formula (A-1) (yield: 80%).

It is to be noted that the structure of the resultant compound was confirmed by $^1$H-NMR (model "JNM-ECA-400" manufactured by JEOL, Ltd.). The results are shown below.

$^1$H-NMR (400 MHz; solvent: DMSO-d$_6$, internal standard: TMS): δ (ppm)=0.91 to 2.50 (26.0H), 2.50 to 3.50 (3.0H), 4.20 to 4.70 (2.0H), 7.70 to 8.30 (15.0H)

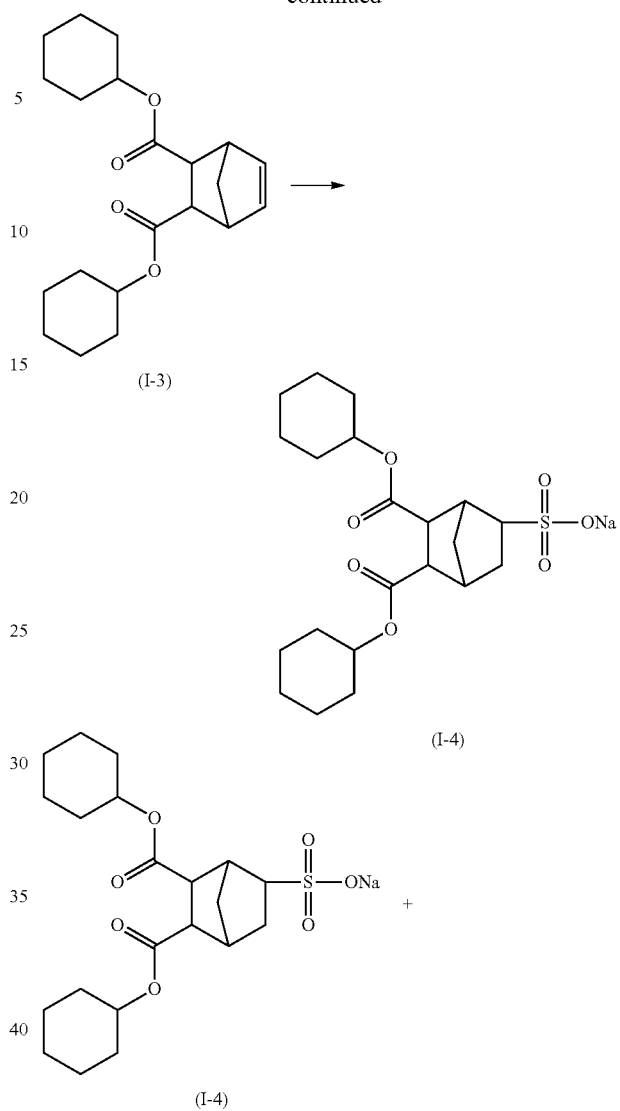
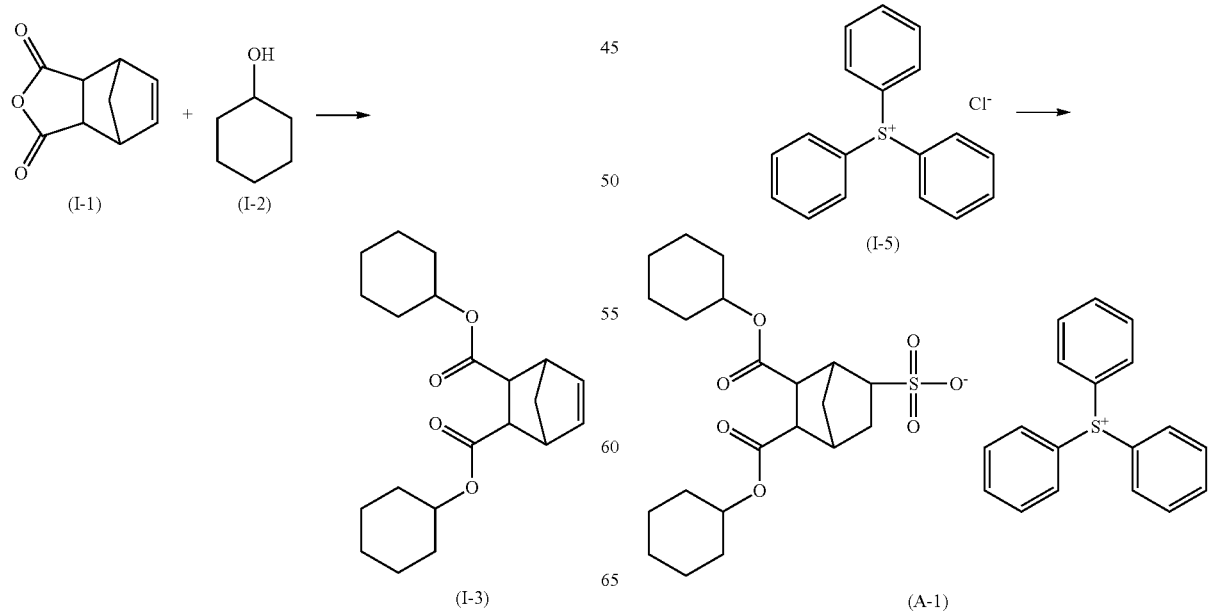

Example 2

Synthesis of (A-2)

A compound (A-2) represented by the following formula (A-2) was obtained in a similar manner to Example 1 except that the compound (I-5) used in Example 1 was changed to a compound (I-6) represented by the following formula (I-6).

(I-6)

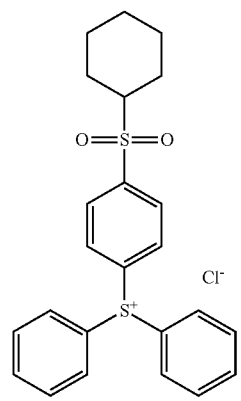

(A-2)

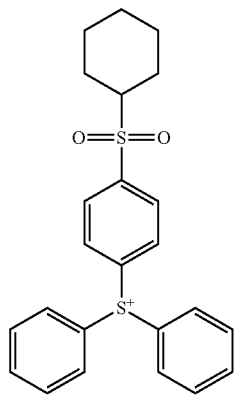

Example 3

Synthesis of (A-3)

A compound (A-3) represented by the following formula (A-3) was obtained in a similar manner to Example 1 except that the compound (I-2) used in Example 1 was changed to a compound (I-7) represented by the following formula (I-7).

(I-7)

(A-3)

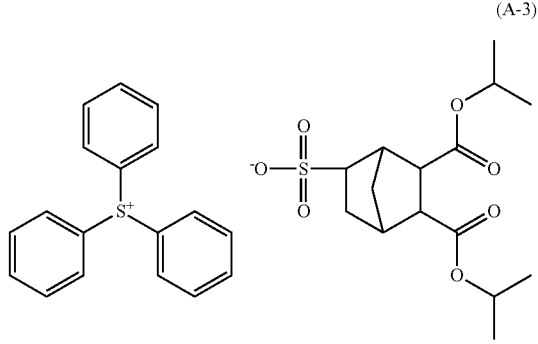

Example 4

Synthesis of (A-4)

A compound (A-4) represented by the following formula (A-4) was obtained in a similar manner to Example 1 except that the compound (I-2) used in Example 1 was changed to a compound (I-8) represented by the following formula (I-8), and the compound (I-5) was changed to the compound (I-6).

(I-8)

(A-4)

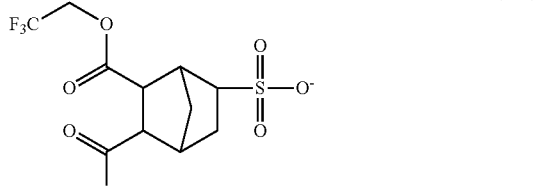

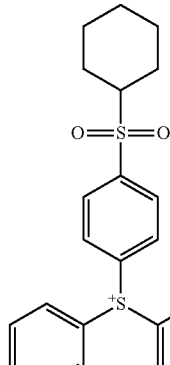

Example 5

Synthesis of (A-5)

A compound (A-5) represented by the following formula (A-5) was obtained in a similar manner to Example 1 except that the compound (I-2) used in Example 1 was changed to a compound (I-9) represented by the following formula (I-9).

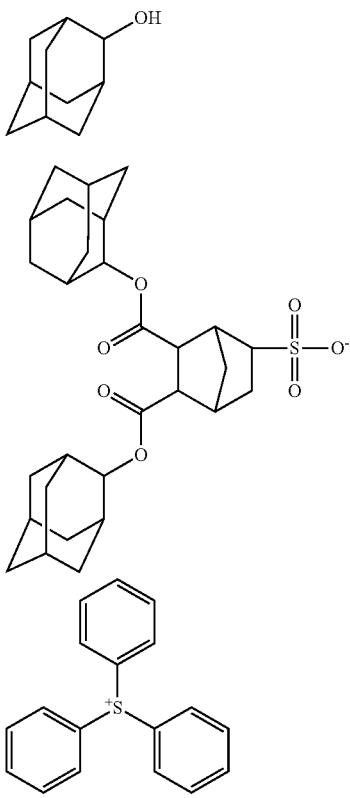

(I-9)

(A-5)

Synthesis of Polymer (B)

Synthesis Example 1

Synthesis of Polymer (B-1)

After 55 g of a compound (M-1) represented by the following formula (M-1), 45 g of a compound (M-2) represented by the following formula (M-2), 4 g of azobisisobutyronitrile and 1 g of t-dodecyl mercaptan were dissolved in 100 g of propylene glycol monomethyl ether, the mixture was subjected to polymerization for 16 hrs under a nitrogen atmosphere while the reaction temperature was maintained at 70° C. After the polymerization, the reaction solution was added dropwise to 1,000 g of n-hexane to permit solidification purification of a copolymer. Next, to the copolymer was added 150 g of propylene glycol monomethyl ether again, and then 150 g of methanol, 34 g of triethylamine and 6 g of water were further added. The mixture was subjected to a hydrolysis reaction for 8 hrs while refluxing at a boiling point. After the reaction, the solvent and the triethylamine were distilled in vacuo, the obtained copolymer was dissolved in 150 g of acetone, which was then added dropwise to 2,000 g water to permit solidification, and the generated white powder was filtered and was dried under a reduced pressure at 50° C. overnight to obtain a polymer (B-1). The obtained polymer (B-1) had the Mw of 10,000 and the Mw/Mn of 2.1, and as a result of the $^{13}$C-NMR analysis, the polymer (B-1) was determined to be a copolymer having a ratio (mol %) of the structural units derived from the compound (M-1) and the compound (M-2) of 65:35.

Synthesis Example 2

Synthesis of Polymer (B-2)

After 53 g of the compound (M-1), 47 g of a compound (M-3) represented by the following formula (M-3), 4 g of azobisisobutyronitrile and 0.2 g of t-dodecyl mercaptan were dissolved in 200 g of propylene glycol monomethyl ether, the mixture was subjected to polymerization for 6 hrs under a nitrogen atmosphere while the reaction temperature was maintained at 70° C. After the polymerization, the reaction solution was added dropwise to 2,000 g of n-hexane to permit solidification purification of a polymer. Next, to the copolymer was added 150 g of propylene glycol monomethyl ether again, and then 150 g of methanol, 37 g of triethylamine and 7 g of water were further added. The mixture was subjected to a hydrolysis reaction for 8 hrs while refluxing at a boiling point. After the reaction, the solvent and the triethylamine were distilled in vacuo, the obtained copolymer was dissolved in 150 g of acetone, which was then added dropwise to 2,000 g water to permit solidification, and the generated white powder was filtered and was dried under a reduced pressure at 50° C. overnight to obtain a polymer (B-2). The obtained copolymer had the Mw of 13,000 and the Mw/Mn of 2.4, and as a result of the $^{13}$C-NMR analysis, the polymer (B-2) was determined to be a copolymer having a ratio (mol %) of each structural unit derived from the compound (M-1) and the compound (M-3) of 50:50.

Synthesis Example 3

Synthesis of Polymer (B-3)

After 55 g of a compound (M-4) represented by the following formula (M-4), 45 g a compound (M-5) represented by the following formula (M-5) and 3 g of azobisisobutyronitrile were dissolved in 300 g of methyl ethyl ketone, the mixture was subjected to polymerization for 6 hrs under a nitrogen atmosphere while the reaction temperature was maintained at 78° C. After the polymerization, the reaction solution was added dropwise to 2,000 g of methanol to solidification a copolymer. Next, the copolymer was washed with 300 g of methanol twice, and the generated white powder was filtered and dried under a reduced pressure at 50° C. overnight. The obtained polymer (B-3) had the Mw of 7,000 and the Mw/Mn of 2.1, and as a result of a $^{13}$C-NMR analysis, the polymer (B-3) was determined to be a copolymer having a ratio (mol %) of each structural unit derived from the compound (M-4) and the compound (M-5) of 52:47.

Synthesis Example 4

Synthesis of Polymer (B-4)

After 20 g of a compound (M-1) represented by the following formula (M-1), 38 g of a compound (M-3) represented by the following formula (M-3), 42 g of a compound (M-7) represented by the following formula (M-7), 5 g of azobisisobutyronitrile and 0.2 g of t-dodecyl mercaptan were dissolved in 100 g of propylene glycol monomethyl ether, the mixture was subjected to polymerization for 16 hrs under a nitrogen atmosphere while the reaction temperature was maintained at 70° C. After the polymerization, the reaction solution was added dropwise to 1,000 g of n-hexane to permit solidification purification of a copolymer. Next, to the copolymer was added 150 g of propylene glycol monomethyl ether again, and then 150 g of methanol, 14 g of triethylamine and 4 g of water were further added. The mixture was subjected to a hydrolysis reaction for 8 hrs while refluxing at a boiling point. After the reaction, the solvent and the triethylamine were distilled in vacuo, the obtained copolymer was dissolved in 150 g of acetone, which was then added dropwise to 2,000 g water to permit solidification, and the generated white powder was filtered and was dried under a reduced pressure at 50° C. overnight to obtain a polymer (B-4). The obtained polymer (B-4) had the Mw of 10,000 and the Mw/Mn of 2.2, and as a result of the $^{13}$C-NMR analysis, the polymer (B-4) was determined to be a copolymer having a ratio (mol %) of the structural units derived from the compounds (M-1), (M-3) and the compound (M-7) of 25:55:20.

Synthesis Example 5

Synthesis of Polymer (B-5)

After 34 g of a compound (M-1) represented by the following formula (M-1), 40 g of a compound (M-6) represented by the following formula (M-6), 26 g of a compound (M-8) represented by the following formula (M-8), 8 g of azobisisobutyronitrile and 3 g of t-dodecyl mercaptan were dissolved in 100 g of propylene glycol monomethyl ether, the mixture was subjected to polymerization for 16 hrs under a nitrogen atmosphere while the reaction temperature was maintained at 70° C. After the polymerization, the reaction solution was added dropwise to 1,000 g of n-hexane to permit solidification purification of a copolymer. Next, to the copolymer was added 150 g of propylene glycol monomethyl ether again, and then 150 g of methanol, 26 g of triethylamine and 7 g of water were further added. The mixture was subjected to a hydrolysis reaction for 8 hrs while refluxing at a boiling point. After the reaction, the solvent and the triethylamine were distilled in vacuo, the obtained copolymer was dissolved in 150 g of acetone, which was then added dropwise to 2,000 g water to permit solidification, and the generated white powder was filtered and was dried under a reduced pressure at 50° C. overnight to obtain a polymer (B-5). The obtained polymer (B-5) had the Mw of 5,000 and the Mw/Mn of 2.0, and as a result of the $^{13}$C-NMR analysis, the polymer (B-5) was determined to be a copolymer having a ratio (mol %) of the structural units derived from the compounds (M-1), (M-6) and the compound (M-8) of 45:35:20.

Synthesis Example 6

Synthesis of Polymer (B-6)

After 23 g of a compound (M-1) represented by the following formula (M-1), 60 g of a compound (M-2) represented by the following formula (M-2), 17 g of a compound (M-9) represented by the following formula (M-9), 4 g of azobisisobutyronitrile, and 0.2 g of t-dodecyl mercaptan were dissolved in 100 g of propylene glycol monomethyl ether, the mixture was subjected to polymerization for 16 hrs under a nitrogen atmosphere while the reaction temperature was maintained at 70° C. After the polymerization, the reaction solution was added dropwise to 1,000 g of n-hexane to permit solidification purification of a copolymer. Next, to the copolymer was added 150 g of propylene glycol monomethyl ether again, and then 150 g of methanol, 16 g of triethylamine and 4 g of water were further added. The mixture was subjected to a hydrolysis reaction for 8 hrs while refluxing at a boiling point. After the reaction, the solvent and the triethylamine were distilled in vacuo, the obtained copolymer was dissolved in 150 g of acetone, which was then added dropwise to 2,000 g water to permit solidification, and the generated white powder was filtered and was dried under a reduced pressure at 50° C. overnight to obtain a polymer (B-6). The obtained polymer (B-6) had the Mw of 10,000 and the Mw/Mn of 2.1, and as a result of the $^{13}$C-NMR analysis, the polymer (B-6) was determined to be a copolymer having a ratio (mol %) of the structural units derived from the compounds (M-1), (M-2) and the compound (M-9) of 30:50:20.

(M-1)

(M-2)

(M-3)

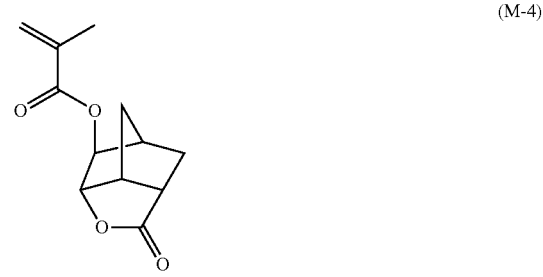

(M-4)

(M-5)

-continued

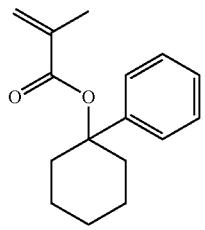
(M-6)

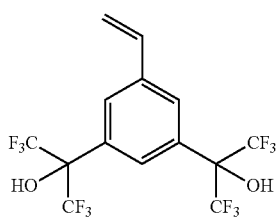
(M-7)

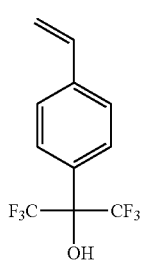
(M-8)

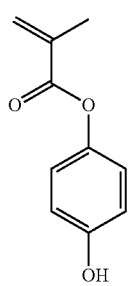
(M-9)

It is to be noted that the weight average molecular weight (Mw) and the number average molecular weight (Mn) in the foregoing Examples were determined by gel permeation chromatography (GPC) using GPC columns manufactured by Tosoh Corporation (G2000HXL×2, G3000HXL×1, and G4000HXL×1) under the analysis conditions including a flow rate of 1.0 mL/min, an elution solvent of tetrahydrofuran and a column temperature of 40° C., with mono-dispersed polystyrene as a standard. Furthermore, the dispersity index Mw/Mn was calculated from the results of the determination. In addition, the $^{13}$C-NMR analysis was carried out using a model "JNM-EX270" manufactured by JEOL, Ltd.

Preparation of Radiation-Sensitive Composition

Example 6

As shown in Table 1, a radiation-sensitive composition solution was prepared by mixing 100 parts by mass of the polymer (B-1) prepared in the Synthesis Examples, 27 parts by mass of the compound (A-1), 1,400 parts by mass/3,300 parts by mass of the solvents (C-1/C-2) and 2 parts by mass of the acid diffusion control agent (D-1), and filtering the resultant mixed liquid through a membrane filter having a pore size of 200 nm.

Examples 7 to 21 and Comparative Examples 1 to 3

Each radiation-sensitive composition of Examples 7 to 21 and Comparative Examples 1 to 3 was prepared by mixing the polymer (B), the compound (A), the solvent (C), and the acid diffusion control agent (D) of the type and the amount charged shown in Table 1, and filtering the resultant mixed liquid through a membrane filter having a pore size of 200 nm.

| | (A) Component | | (B) Polymer | | (C) Solvent | | (D) Acid diffusion control agent | |
|---|---|---|---|---|---|---|---|---|
| | type | amount blended parts by mass | type | amount blended (parts by mass) | type | amount blended (parts by mass) | type | amount blended (parts by mass) |
| Example 6 | A-1 | 27 | B-1 | 100 | C-1 C-2 | 1,400 3,300 | D-1 | 2 |
| Example 7 | A-2 | 27 | B-1 | 100 | C-1 C-2 | 1,400 3,300 | D-2 | 2.5 |
| Example 8 | A-3 | 27 | B-1 | 100 | C-1 C-2 | 1,400 3,300 | D-1 | 2 |
| Example 9 | A-2 | 27 | B-2 | 100 | C-1 C-2 | 1,400 3,300 | D-2 | 2.5 |
| Example 10 | A-1 | 27 | B-2 | 100 | C-1 C-2 | 3,300 1,400 | D-3 | 2 |
| Example 11 | A-2 | 27 | B-4 | 100 | C-1 C-2 | 3,300 1,400 | D-2 | 2.5 |
| Example 12 | A-3 | 27 | B-4 | 100 | C-1 C-2 | 3,300 1,400 | D-4 | 2.5 |
| Example 13 | A-1 | 27 | B-5 | 100 | C-1 C-2 | 3,300 1,400 | D-2 | 2.5 |
| Example 14 | A-2 | 27 | B-5 | 100 | C-1 C-2 | 3,300 1,400 | D-4 | 2.5 |
| Example 15 | A-1 a-1 | 7 7 | B-3 | 100 | C-2 C-3 | 2,600 1,300 | D-1 | 4 |
| Example 16 | A-2 a-1 | 7 7 | B-3 | 100 | C-2 C-3 | 2,600 1,300 | D-2 | 10 |
| Example 17 | A-2 a-1 | 7 7 | B-6 | 100 | C-2 C-3 | 2,600 1,300 | D-4 | 2.5 |
| Example 18 | A-4 | 27 | B-1 | 100 | C-1 C-2 | 1,400 3,300 | D-2 | 2.5 |
| Example 19 | A-5 | 27 | B-1 | 100 | C-1 C-2 | 1,400 3,300 | D-2 | 2.5 |
| Example 20 | A-4 | 27 | B-4 | 100 | C-1 C-2 | 1,400 3,300 | D-2 | 2.5 |
| Example 21 | A-5 | 27 | B-5 | 100 | C-1 C-2 | 1,400 3,300 | D-4 | 2.5 |
| Comparative Example 1 | a-1 | 27 | B-1 | 100 | C-1 C-2 | 1,400 3,300 | D-1 | 2 |
| Comparative Example 2 | a-2 | 27 | B-1 | 100 | C-1 C-2 | 3,300 1,400 | D-1 | 2 |
| Comparative Example 3 | a-1 | 14 | B-3 | 100 | C-2 C-3 | 2,600 1,300 | D-1 | 4 |

Details of the component (A), the component (C) and the acid diffusion control agent (D) shown in Table 1 are collectively presented below.

Component (A)

Compounds represented by the following formulae (A-1) to (A-5), (a-1) and (a-2):

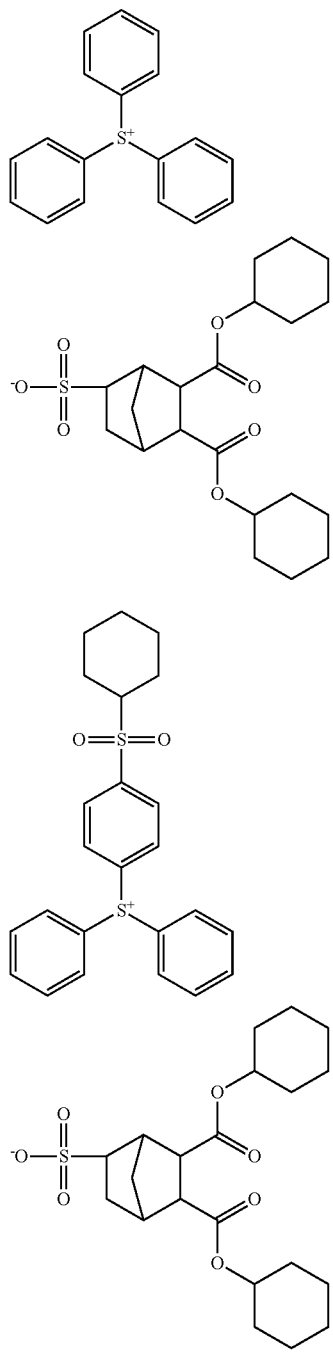
(A-1)
(A-2)
(A-3)
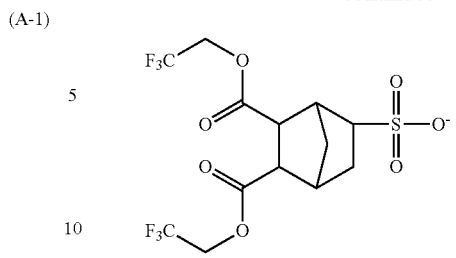
(A-4)
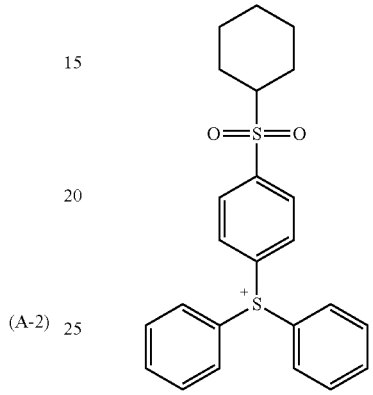
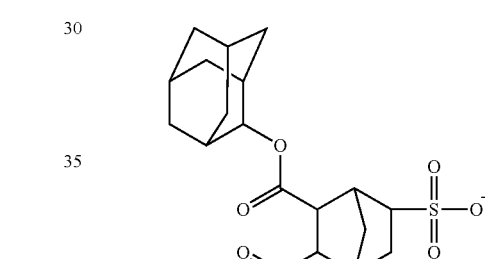
(A-5)
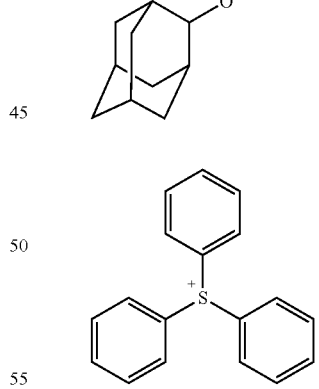
(a-1)
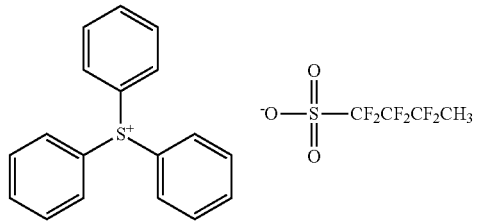

-continued

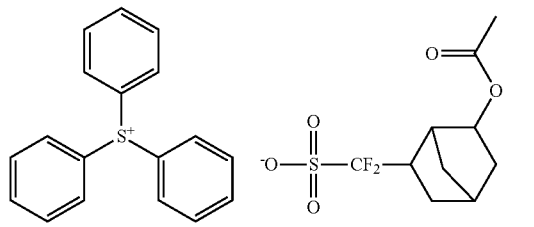

(a-2)

Component (C)
  (C-1): ethyl lactate
  (C-2): propylene glycol monomethyl ether acetate
  (C-3): cyclohexanone
Acid Diffusion Control Agent (D)
  (D-1): tri-n-octylamine
  (D-2): compound represented by the following formula (D-2)
  (D-3): N-tert-butoxycarbonyl-2-phenylbenzimidazole
  (D-4): compound represented by the following formula (D-4)

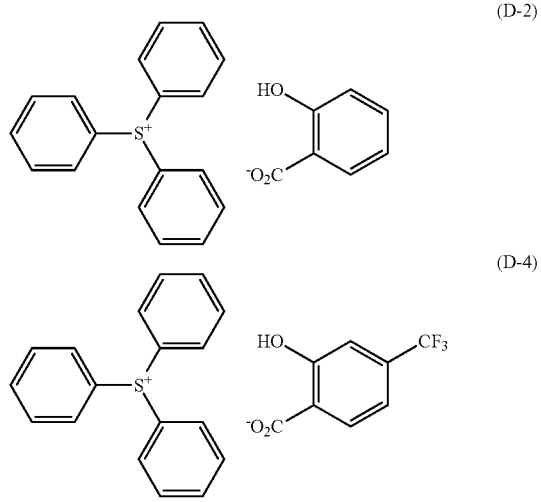

Evaluation (Evaluation of EB exposure)

After each solution of the radiation-sensitive composition (radiation-sensitive compositions of Examples 6 to 14, 18 to 21 and Comparative Examples 1 to 2) was spin-coated on a silicon wafer in "CLEAN TRACK ACT-8" manufactured by Tokyo Electron Limited, PB (i.e., heating treatment) was carried out under the condition shown in Table 2 to form a resist film having a film thickness of 50 nm. Thereafter, the resist film was irradiated with an electron beam using a simplified electron beam drawing apparatus (manufactured by Hitachi, Ltd., model "HL800D"; output: 50 KeV, electric current density: 5.0 ampere/cm$^2$). After the irradiation with an electron beam, PEB was carried out under the condition shown in Table 2. Thereafter, development was carried out at 23° C. for 1 min by a puddling method using a 2.38% by mass aqueous tetramethylammonium hydroxide solution, followed by washing with pure water, drying to form a resist pattern.

With regard to the resist patterns formed in this manner, each test of evaluations was conducted, and the results of the evaluations are shown in Table 2.

Sensitivity (L/S)

An exposure dose at which a pattern (line and space pattern (1L 1S) as generally referred to) configured with a line part having a line width of 130 nm and a space part (i.e., groove) formed by neighboring line parts with an interval of 130 nm was formed to give a line width of 1:1 was defined as "optimal exposure dose", and the "sensitivity" (μC/cm$^2$) was evaluated based on the "optimal exposure dose".

Nanoedge Roughness (i)

A line pattern of the line and space pattern (1L 1S) having a line width of 130 nm as designed was observed using a scanning electron microscope for semiconductors (high resolution semiconductor FEB length measuring apparatus, trade name "S-9220", manufactured by Hitachi, Ltd.). The line width (nm) was determined at arbitrary ten points, and the variance of the measurements expressed as a value in terms of the 3 Sigma was defined as nanoedge roughness (nm). The smaller value of the nanoedge roughness indicates the more favorable linearity of the pattern.

Resolution (L/S)

With respect to the line and space pattern (1L 1S), the minimum line width (nm) in the line pattern resolved at the optimal exposure dose was defined as resolution.

Evaluation (ArF Exposure Evaluation)

A coating film having a film thickness of 75 nm was provided using the solution of each radiation-sensitive composition (radiation-sensitive compositions of Examples 15 to 17 and Comparative Example 3) on a 12 inch silicon wafer on which an underlayer antireflective film ("ARC66", manufactured by Nissan Chemical Industries, Ltd.) had been formed, and PB was carried out under the condition shown in Table 3. Next, a composition for forming an upper layer film described in Example 1 of WO 2008/047678 was spin-coated on the provided coating film, and PB was carried out at 90° C. for 60 sec to form a coated film having a film thickness of 90 nm. The coating film was subjected to reduced projection exposure through a mask pattern using an ArF excimer laser Immersion Scanner ("NSR S610C", manufactured by NIKON Corporation) under a condition involving NA of 1.3, a ratio of 0.800, with "Annular". After the exposure, PEB was carried out under the condition shown in Table 3. Thereafter, development was carried out with a 2.38% by mass aqueous tetramethylammonium hydroxide solution, followed by washing with water and drying to form a positive type resist pattern.

With respect to the resist pattern formed in such a manner, each test of evaluations was carried out, and the results of the evaluations are shown in Table 3.

MEEF (Mask Error Enhancement Factor)

An exposure dose at which a line and space (LS) pattern having a line width of 50 nm was formed by an exposure through a 1L/1S mask pattern with a target size of 50 nm under the condition of evaluation was defined as an optimum exposure dose. Next, an LS pattern having a pitch of 100 nm was formed at the optimal exposure dose using each mask pattern with a target size of the line width of 46 nm, 48 nm, 50 nm, 52 nm or 54 nm, and the line width formed on the resist film was measured with an SEM for line-width measurement (CG4000, manufactured by Hitachi, Ltd.).

In this procedure, the line width (nm) formed on the resist film using each mask pattern was plotted along the ordinate with respect to the target size (nm) along the abscissa, and the slope of the resulting straight line was determined as MEEF.

It is to be noted that the smaller MEEF value is evaluated as being superior since costs for producing a mask can be reduced.

Nanoedge Roughness (ii)

An exposure dose at which a resist pattern having a line width of 50 nm was formed by an exposure through a 1L/1.8S mask pattern with a target size of 50 nm under the condition of evaluation was defined as an optimum exposure dose. When the 1L/1.8S pattern with a target size of 50 nm obtained at the optimum exposure dose was observed, the line width (nm) was determined at arbitrary ten points upon observation from above the pattern using a Critical Dimension Measurement scanning electron microscope (SEM): CG4000 manufactured by Hitachi, Ltd., and the variance of the measurements expressed as a value in terms of the 3 Sigma was defined as nanoedge roughness (nm). It is to be noted that the smaller value of the nanoedge roughness indicates the more favorable linearity of the pattern.

Minimum Collapse Dimension

An exposure was carried out through a 1L/1.85 mask pattern with a target size of 50 nm while changing the exposure dose by 1 mJ under the condition of evaluation. The line width (nm) of the pattern formed at an exposure dose less than the exposure dose at which the line collapse occurred by 1 mJ was measured with the SEM for line-width measurement (manufactured by Hitachi, Ltd., model: CG4000). The line width measured was defined as a minimum collapse dimension. It is to be noted that the smaller value of the minimum collapse dimension indicates the higher pattern collapse resistance.

TABLE 2

| | PB condition | | PEB condition | | | Nano-edge | |
|---|---|---|---|---|---|---|---|
| | Temperature (°C.) | time (sec) | Temperature (°C.) | time (sec) | Sensitivity ($\mu C/cm^2$) | roughness (i) (nm) | Resolution (nm) |
| Example 6 | 110 | 60 | 120 | 60 | 42.0 | 12 | 70 |
| Example 7 | 110 | 60 | 120 | 60 | 43.0 | 10 | 60 |
| Example 8 | 110 | 60 | 120 | 60 | 42.0 | 11 | 70 |
| Example 9 | 110 | 60 | 140 | 60 | 40.0 | 9 | 60 |
| Example 10 | 110 | 60 | 140 | 60 | 42.0 | 11 | 70 |
| Example 11 | 110 | 60 | 140 | 60 | 39.0 | 9 | 60 |
| Example 12 | 110 | 60 | 140 | 60 | 40.0 | 10 | 50 |
| Example 13 | 110 | 60 | 110 | 60 | 39.0 | 9 | 50 |
| Example 14 | 110 | 60 | 110 | 60 | 39.0 | 8 | 50 |
| Example 18 | 110 | 60 | 125 | 60 | 41.0 | 9 | 60 |
| Example 19 | 110 | 60 | 125 | 60 | 41.0 | 10 | 60 |
| Example 20 | 110 | 60 | 145 | 60 | 40.0 | 10 | 60 |
| Example 21 | 110 | 60 | 115 | 60 | 39.0 | 9 | 60 |
| Comparative Example 1 | 110 | 60 | 100 | 60 | 42.0 | 15 | 90 |
| Comparative Example 2 | 110 | 60 | 100 | 60 | 43.0 | 16 | 90 |

TABLE 3

| | PB condition | | PEB condition | | | Nano-edge roughness (ii) (nm) | Minimum collapse dimension (nm) |
|---|---|---|---|---|---|---|---|
| | Temperature (°C.) | time (sec) | Temperature (°C.) | time (sec) | MEEF | | |
| Example 15 | 110 | 60 | 120 | 60 | 3.3 | 5.2 | 36 |
| Example 16 | 110 | 60 | 120 | 60 | 3.4 | 4.9 | 35 |
| Example 17 | 110 | 60 | 120 | 60 | 3.4 | 5.1 | 35 |
| Comparative Example 3 | 110 | 60 | 120 | 60 | 4.1 | 7.0 | 42 |

As is clear from Table 2 and Table 3, the radiation-sensitive compositions of Examples 6 to 21 containing the compound (A), (A-1) to (A-5), as the acid generating agent were more efficaciously sensitive to electron beams or extreme ultraviolet rays as compared with the radiation-sensitive compositions of Comparative Examples 1 to 3 not containing any of the acid generating agents (A-1) to (A-5), accompanied by lower roughness and superior resolution. In addition, the radiation-sensitive compositions of Examples 6 to 21 enabled a chemically amplified positive type resist film to be formed that is capable of forming a fine pattern with high accuracy and in a stable manner.

The radiation-sensitive composition of the embodiment of the present invention is efficaciously sensitive to (extreme) far ultraviolet rays such as a KrF excimer laser, an ArF excimer laser and EUV, X-rays such as a synchrotron radioactive ray, and electron beams, superior in nanoedge roughness, sensitivity and resolution, and capable of forming a fine pattern with high accuracy and in a stable manner. Therefore, the radiation-sensitive composition of the embodiment of the present invention is suitably used for producing semiconductor devices in which further progress of miniaturization is expected in the future.

Obviously, numerous modifications and variations of the present invention are possible in light of the above teachings. It is therefore to be understood that within the scope of the appended claims, the invention may be practiced otherwise than as specifically described herein.

What is claimed is:

1. A radiation-sensitive composition comprising:
a compound represented by a formula (1-A-1), a compound represented by a formula (1-B-1), or both thereof; and
a polymer comprising a structural unit that comprises an acid-labile group:

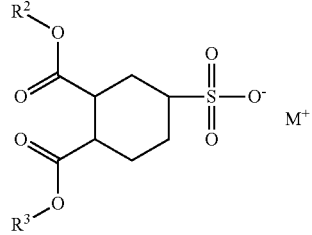

(1-A-1)

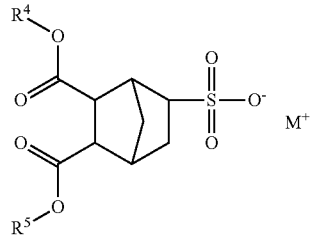

(1-B-1)

wherein, in the formulae (1-A-1) and (1-B-1),
$M^+$ is a monovalent onium cation; and
$R^2$, $R^3$, $R^4$ and $R^5$ each independently represent a linear or branched hydrocarbon group having 1 to 30 carbon atoms, an alicyclic hydrocarbon group having 3 to 30 carbon atoms, an aromatic hydrocarbon group having 6 to 30 carbon atoms, or a heterocyclic group having 4 to 30 carbon atoms, wherein a part or all of hydrogen atoms included in the linear or branched hydrocarbon group having 1 to 30 carbon atoms are substituted with at least one of an aromatic hydrocarbon group or an alicyclic hydrocarbon group, wherein the linear or branched hydrocarbon group having 1 to 30 carbon atoms does not include or includes an ester group, an amide group, a urethane group, a urea group, a carbonate group or a sulfide group between carbon atoms, and wherein a part or all of hydrogen atoms included in the alicyclic hydrocarbon group, the aromatic hydrocarbon group and the heterocyclic group represented by $R^2$, $R^3$, $R^4$ and $R^5$ are not substituted or substituted.

2. The radiation-sensitive composition according to claim 1, wherein the polymer further comprises a structural unit represented by a formula (b-1), a structural unit represented by a formula (b-2) or a combination thereof:

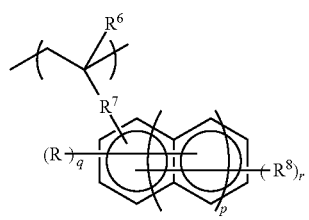
(b-1)

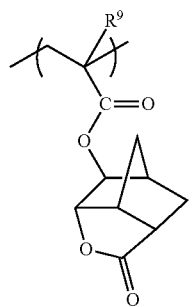
(b-2)

wherein, in the formula (b-1), $R^6$ represents a hydrogen atom or a methyl group; $R^7$ represents a single bond, —CO—O—, or —CO—NH—; $R^8$ represents a linear or branched alkyl group having 1 to 12 carbon atoms, a linear or branched alkoxyl group having 1 to 12 carbon atoms, or an acyloxy group having 2 to 12 carbon atoms; R represents a hydroxyl group, or a group that comprises a hydroxyl group or a hydroxyl group; p is 0 or 1; q and r are each independently an integer of 0 to 3, wherein, in a case where p is 0, a sum of q and r is no greater than 5, and in a case where $R^8$ is present in a plurality of number, a plurality of $R^8$s are identical or different, and in the formula (b-2), $R^9$ represents a hydrogen atom or a methyl group.

3. The radiation-sensitive composition according to claim 1, wherein the radiation-sensitive composition further comprises a solvent, wherein the solvent comprises an ethylene glycol monoalkyl ether acetate, a propylene glycol monoalkyl ether acetate or a combination thereof, and a content of the ethylene glycol monoalkyl ether acetate, the propylene glycol monoalkyl ether acetate or the combination thereof in the solvent is no less than 70% by mass.

4. A compound represented by a formula (1-A-1) or (1-B-1):

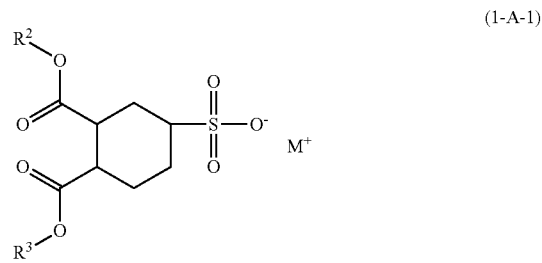
(1-A-1)

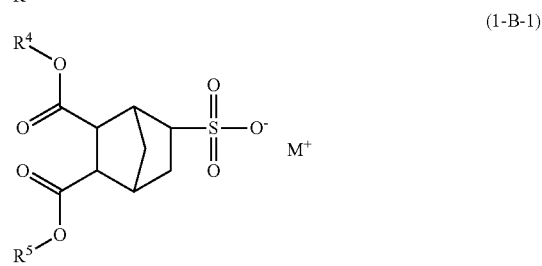
(1-B-1)

wherein, in the formulae (1-A-1) and (1-B-1), $M^+$ is a monovalent onium cation; and $R^2$, $R^3$, $R^4$ and $R^5$ each independently represent a linear or branched hydrocarbon group having 1 to 30 carbon atoms, an alicyclic hydrocarbon group having 3 to 30 carbon atoms, an aromatic hydrocarbon group having 6 to 30 carbon atoms, or a heterocyclic group having 4 to 30 carbon atoms, wherein a part or all of hydrogen atoms included in the linear or branched hydrocarbon group having 1 to 30 carbon atoms are substituted with at least one of an aromatic hydrocarbon group or an alicyclic hydrocarbon group, wherein the linear or branched hydrocarbon group having 1 to 30 carbon atoms does not include or includes an ester group, an amide group, a urethane group, a urea group, a carbonate group or a sulfide group between carbon atoms, and wherein a part or all of hydrogen atoms included in the alicyclic hydrocarbon group, the aromatic hydrocarbon group and the heterocyclic group represented by $R^2$, $R^3$, $R^4$ and $R^5$ are not substituted or substituted.

5. The radiation-sensitive composition according to claim 1, wherein the alicyclic hydrocarbon group represented by $R^2$, $R^3$, $R^4$ and $R^5$ is a cyclopropyl group, a cyclobutyl group, a cyclopentyl group, a cyclohexyl group, a bornyl group, a norbornyl group, an adamantyl group, a pinanyl group, a thuiyl group, a caryle group, or a camphonyl group, a part or all of hydrogen atoms included in the alicyclic hydrocarbon group being not substituted or substituted.

6. The radiation-sensitive composition according to claim 1, wherein the aromatic hydrocarbon group represented by $R^2$, $R^3$, $R^4$ and $R^5$ is a phenyl group, a 1-naphthyl group, a 2-naphthyl group, a 1-anthryl group, or a 1-phenanthryl group, a part or all of hydrogen atoms included in the aromatic hydrocarbon group being not substituted or substituted.

7. The compound according to claim 4, wherein the alicyclic hydrocarbon group represented by $R^2$, $R^3$, $R^4$ and $R^5$ is a cyclopropyl group, a cyclobutyl group, a cyclopentyl group, a cyclohexyl group, a bornyl group, a norbornyl group, an adamantyl group, a pinanyl group, a thuiyl group, a caryle group, or a camphonyl group, a part or all of hydrogen atoms included in the alicyclic hydrocarbon group being not substituted or substituted.

8. The compound according to claim 4, wherein the aromatic hydrocarbon group represented by $R^2$, $R^3$, $R^4$ and $R^5$ is a phenyl group, a 1-naphthyl group, a 2-naphthyl group, a 1-anthryl group, or a 1-phenanthryl group, a part or all of hydrogen atoms included in the aromatic hydrocarbon group being not substituted or substituted.

* * * * *